US009918989B2

(12) United States Patent
Luckhart et al.

(10) Patent No.: US 9,918,989 B2
(45) Date of Patent: Mar. 20, 2018

(54) COMBINATION THERAPIES FOR MALARIA

(71) Applicant: The Regents of the University of California, Oakland, CA (US)

(72) Inventors: Shirley Luckhart, Davis, CA (US); Cecilia Giulivi, Davis, CA (US)

(73) Assignee: The Regents Of The University Of California, Oakland, CA (US)

( * ) Notice: Subject to any disclaimer, the term of this patent is extended or adjusted under 35 U.S.C. 154(b) by 0 days.

(21) Appl. No.: 14/904,673

(22) PCT Filed: Jul. 11, 2014

(86) PCT No.: PCT/US2014/046440
§ 371 (c)(1),
(2) Date: Jan. 12, 2016

(87) PCT Pub. No.: WO2015/006752
PCT Pub. Date: Jan. 15, 2015

(65) Prior Publication Data
US 2016/0151379 A1    Jun. 2, 2016

Related U.S. Application Data

(60) Provisional application No. 61/923,405, filed on Jan. 3, 2014, provisional application No. 61/845,920, filed on Jul. 12, 2013.

(51) Int. Cl.
| | |
|---|---|
| *A61K 39/00* | (2006.01) |
| *A61K 31/5377* | (2006.01) |
| *A61K 45/06* | (2006.01) |
| *A61K 31/4162* | (2006.01) |
| *G01N 33/569* | (2006.01) |
| *A61K 31/416* | (2006.01) |
| *A61K 31/4439* | (2006.01) |
| *A61K 49/00* | (2006.01) |
| *C12Q 1/48* | (2006.01) |
| *G01N 33/50* | (2006.01) |
| *G01N 33/573* | (2006.01) |
| *A61K 31/4035* | (2006.01) |
| *A61K 31/404* | (2006.01) |
| *A61K 31/407* | (2006.01) |
| *A61K 31/4168* | (2006.01) |
| *A61K 31/4178* | (2006.01) |
| *A61K 31/473* | (2006.01) |
| *A61K 31/52* | (2006.01) |
| *A61K 31/541* | (2006.01) |

(52) U.S. Cl.
CPC ........ *A61K 31/5377* (2013.01); *A61K 31/404* (2013.01); *A61K 31/407* (2013.01); *A61K 31/4035* (2013.01); *A61K 31/416* (2013.01); *A61K 31/4162* (2013.01); *A61K 31/4168* (2013.01); *A61K 31/4178* (2013.01); *A61K 31/4439* (2013.01); *A61K 31/473* (2013.01); *A61K 31/52* (2013.01); *A61K 31/541* (2013.01); *A61K 45/06* (2013.01); *A61K 49/0008* (2013.01); *C12Q 1/485* (2013.01); *G01N 33/5008* (2013.01); *G01N 33/5014* (2013.01); *G01N 33/56905* (2013.01); *G01N 33/573* (2013.01); *G01N 2333/445* (2013.01); *G01N 2333/912* (2013.01); *G01N 2440/14* (2013.01); *G01N 2500/04* (2013.01); *G01N 2500/10* (2013.01); *G01N 2500/20* (2013.01)

(58) Field of Classification Search
CPC ..... A61K 39/00; A61K 39/002; A61K 39/015
USPC .......................................... 424/265.1, 268.1
See application file for complete search history.

(56) References Cited

U.S. PATENT DOCUMENTS

| | | |
|---|---|---|
| 7,670,631 B2 | 3/2010 | Mota et al. |
| 2009/0192127 A1 | 7/2009 | Scheuring et al. |
| 2011/0251246 A1 | 10/2011 | Kufe et al. |
| 2016/0151380 A1 | 6/2016 | Luckhart et al. |

FOREIGN PATENT DOCUMENTS

| | | | |
|---|---|---|---|
| WO | 2008/022422 A1 | | 2/2008 |
| WO | 2008/094737 A2 | | 8/2008 |
| WO | 2010/049173 A1 | | 5/2010 |
| WO | WO2010/049173 | * | 5/2010 |
| WO | 2015/006753 A2 | | 1/2015 |

OTHER PUBLICATIONS

Dluzewski, A.R., et al. Experientia (Basel), vol. 52, No. 6, pp. 621-623, 1996.*
Anand et al., "The Specific, Reversible JNK Inhibitor Sp600125 Improves Survivability and Attenuates Neuronal Cell Death in Experimental Cerebral Malaria (ECM)", Parasitol Res, vol. 112, 2013, pp. 1959-1966.
Brumlik et al., "Human p38 Mitogen-Activated Protein Kinase Inhibitor Drugs Inhibit Plasmodium falciparum Replication", Exp Parasitol, vol. 128, No. 2, 2011, pp. 170-175.
Burrows et al., "Designing the Next Generation of Medicines for Malaria Control and Eradication", Malaria Journal, vol. 12, No. 187, 2013, pp. 1-20.
Corby-Harris et al., "Activation of Akt Signaling Reduces the Prevalence and Intensity of Malaria Parasite Infection and Lifespan in *Anopheles stephensi* Mosquitoes", PLoS Pathogens, vol. 6, No. 7, 2010, pp. 1-10.
Delves et al., "The Activities of Current Antimalarial Drugs on the Life Cycle Stages of Plasmodium: A Comparative Study with Human and Rodent Parasites", PLoS Medicine, vol. 9, No. 2, 2012, pp. 1-14.

(Continued)

*Primary Examiner* — Rodney P Swartz
(74) *Attorney, Agent, or Firm* — Morrison & Foerster LLP

(57) ABSTRACT

The present disclosure provides methods for treating or preventing malaria by administration of a protein kinase inhibitor and optionally one or both of a further protein kinase inhibitor and an antimalarial drug to a mammalian subject infected with or at risk of exposure to *Plasmodium* sp. In some aspects, the therapeutic and prophylactic regimens of the present disclosure are effective in reducing parasite development in mosquitoes feeding on recipients of the regimens. Additionally, the present disclosure provides methods for screening candidate antimalarial agents.

34 Claims, 10 Drawing Sheets

(56) References Cited

OTHER PUBLICATIONS

Drexler et al., "Human IGF1 Extends Lifespan and Enhances Resistance to Plasmodium falciparum Infection in the Malaria Vector Anopheles stephensi", The Journal of Experimental Biology, vol. 216, No. 2, 2013, pp. 208-217.
Faye et al., "Multicentre Study Evaluating the Non-Inferiority of the New Paediatric Formulation of Artesunate/Amodiaquine Versus Artemether/Lumefantrine for the Management of Uncomplicated *Plasmodium falciparum* Malaria in Children in Cameroon, Ivory Coast and Senegal", Malaria Journal, vol. 11, No. 433, 2012, pp. 1-8.
Horton, "The Mitogen-Activated Protein Kinome from Anopheles gambiae: Identification, Phylogeny and Functional Characterization of the ERK, JNK and p38 MAP Kinases", BMC Genomics, vol. 12, No. 574, 2011, pp. 1-13.
International Preliminary Report on Patentability received for PCT Patent Application No. PCT/US2014/046440, dated Jan. 21, 2016, 14 pages.
International Search Report and Written Opinion received for PCT Patent Application No. PCT/US2014/046440, dated Oct. 15, 2014, 17 pages.
Jean et al., "Molecular Vehicles for Mitochondrial Chemical Biology and Drug Delivery", ACS Chemical Biology, vol. 9, 2014, pp. 323-333.
Luckhart et al., "Host-Pathogen Interactions in Malaria: Cross-Kingdom Signaling and Mitochondrial Regulation", Current Opinion in Immunology, vol. 36, 2015, pp. 73-79.
Luckhart et al., "Sustained Activation of Akt Elicits Mitochondrial Dysfunction to Block Plasmodium falciparum Infection in the Mosquito Host", PLOS Pathogen, vol. 9, 2013, pp. 1-24.
"Methods for Surveillance of Antimalarial Drug Efficacy", Publications of the World Health Organization: Geneva Switzerland, 2009, 90 pages.
Millholland et al., "A Host GPCR Signaling Network Required for the Cytolysis of Infected Cells Facilitates Release of Apicomplexan Parasites", Cell Host & Microbe, vol. 13, 2013, pp. 15-28.
Pakpour et al., "Ingested Human Insulin Inhibits the Mosquito NF-kB-Dependent Immune Response to Plasmodium falciparum", Infection and Immunity, vol. 80, No. 6, 2012, pp. 2141-2149.
Pakpour et al., "Protein Kinase C-Dependent Signaling Controls the Midgut Epithelial Barrier to Malaria Parasite Infection in Anopheline Mosquitoes", PLOS One, vol. 8, No. 10, 2013, pp. 1-12.
Schwartz, "Prophylaxis of Malaria", Mediterranean Journal of Hematology and Infectious Diseases, vol. 4, 2012, 12 pages.
Surachetpong et al., "MAPK ERK Signaling Regulates the TGF-β1-Dependent Mosquito Response to Plasmodium falciparum", PLOS, Pathogens, vol. 5, No. 4, 2009, pp. 1-11.
Yamamato et al., "Artificial Activation of Mature Unfertilized Eggs in the Malaria Vector Mosquito, *Anopheles stephensi* (Diptera, Culicidae)", Journal of Experimental Biology, vol. 216, 2013, pp. 2960-2966.

\* cited by examiner

FIG. 1A

| Product Description | CAS Number | M.W. | Cell Permeable | ATP-competitive | Reversibility | Structure | IC50 | PubChem Compound ID# | Human Kinome Branch |
|---|---|---|---|---|---|---|---|---|---|
| Bisindolylmaleimide IV | 119139-23-0 | 327.3 | Yes | Yes | Yes | 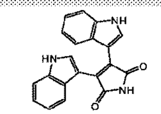 | $IC_{50}$ = 87 nM for PKC | 2389 | AGC |
| Chelerythrine Chloride | 3895-92-9 | 383.8 | Yes | No | unknown | 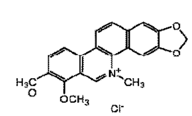 | $IC_{50}$ = 660 nM for PKC | 72311 | AGC |
| Gö 6976 | 136194-77-9 | 378.4 | Yes | Yes | Yes | 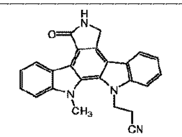 | $IC_{50}$ = 7.9 nM for PKC, rat brain $IC_{50}$ = 2.3 nM for Ca2+-dependent PKC α-isozyme $IC_{50}$ = 6.2 nM for PKCβI | 3501 | AGC |
| Gö 6983 | 133053-19-7 | 442.5 | Yes | Yes | Yes | 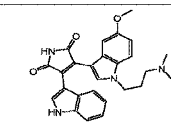 | $IC_{50}$ = 7 nM for PKCα and PKCβ    $IC_{50}$ = 6 nM for PKCγ $IC_{50}$ = 10 nM for PKCδ $IC_{50}$ = 60 nM for PKCζ | 3492 | AGC |
| PKCβII/EGFR Inhibitor | 145915-60-2 | 365.3 | Yes | Yes | Yes | 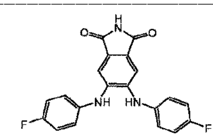 | $IC_{50}$ = 700 nM, 1.9 μM, 3.8 μM, and 410 nM for EGFR and PKC isozymes α, βI, and βII respectively. | 6711154 | TK, AGC |
| PKCβ Inhibitor | 257879-35-9 | 411.5 | Yes | Yes | Yes | 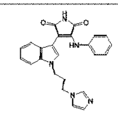 | $IC_{50}$ = 5 nM and 21 nM for human PKCβII and βI $IC_{50}$ = 331 nM, > 1 μM, and 2.8 μM for PKCα, γ, & ε, respectively. | 6419755 | AGC |
| Staurosporine, N-benzoyl- | 120685-11-2 | 570.6 | Yes | Yes | Yes | 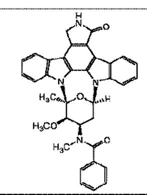 | $IC_{50}$ = 22 nM, 50 nM, 86 nM, 95 nM, 160 nM, 330 nM, 390 nM, 528 nM, 570 nM, 600 nM, 780 nM, 800 nM, 912 nM, and 1.0 μM for PKC (a, b and g), PDGFRb, VEGFR2, Syk, PKCh, PKCd, Flk-1, Flt3, Cdk1/B, PKA, c-Kit, c-Fgr, c-Src, VEGFR1, and EGFR, respectively. $IC_{50}$ = 10000 nM for Ins-R and | 167780527 | AGC, CMGC, TK |

FIG. 1B

| | | | | | | | | |
|---|---|---|---|---|---|---|---|---|
| Staurosporine, Streptomyces sp. | 62996-74-1 | 466.5 | Yes | Yes | Yes | | $IC_{50}$= 20 nM for CaM kinase<br>$IC_{50}$= 0.7 nM for PKC<br>$IC_{50}$= 1.3 nM for MLCK<br>$IC_{50}$= 8.5 nM for PKG<br>$IC_{50}$=7 nM for PKA | 551195 | AGC, CAMK, TK |
| Bisindolylmaleimide III, Hydrochloride | 137592-43-9 | 420.9 | Yes | Yes | Yes | | $IC_{50}$ = 26 nM for protein kinase C. | 16760314 | AGC |
| Gö 7874, Hydrochloride | 287935-76-6 | 507 | Yes | Yes | Yes | 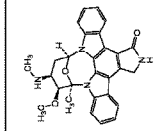 | $IC_{50}$ = 4 nM for rat brain PKC. | 11549733 | AGC |
| H-8, Dihydrochloride | 113276-94-1 | 338.3 | Yes | Yes | Yes | | $K_i$ = 1.2 μM for protein kinase A.<br>$K_i$ = 68 μM for myosin light chain kinase.<br>$K_i$ = 15 μM for protein kinase C.<br>$K_i$ = 490 μM for protein kinase G | 152684 | AGC |
| HA 1004, Dihydrochloride | 92564-34-6 | 366.3 | Yes | Yes | Yes | 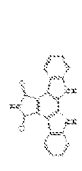 | $K_i$ = 13 μM for myosin light chain kinase.<br>$K_i$ = 150 μM for protein kinase G | 16790499 | AGC |
| MEK1/2 Inhibitor II | 212831-61-3 | 476.2 | Yes | No | Yes | | $IC_{50}$ = 8 nM for MEK1/2. | 9905837 | STE |
| PD98059 | 167869-21-8 | 267.3 | Yes | No | Yes | | IC50 = 2-7 μM | 4713 | STE |
| U0126 | 109511-58-2 | 403.5 | Yes | No | Yes | 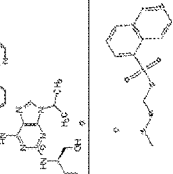 | IC50 = 72 nM for MEK1, 58 nM for MEK2 | 16200066 | STE |
| p38 MAP Kinase Inhibitor IV, JX401 | 1638-41-1 | 456.9 | Yes | Yes | Yes | | $IC_{50}$ = 130 nM for p38a MAPK.<br>$IC_{50}$ = 550 nM and p38b MAPK. | 38164192 | STE |
| p38 MAP Kinase Inhibitor VI, SD-169 | 349087-34-9 | 355.5 | Yes | No | Yes | 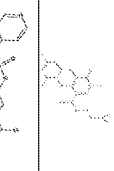 | $IC_{50}$ = 32 nM for MAPK p38a. | 1120109 | STE |
| p38 MAP Kinase Inhibitor VII, SD-169 | 1670-87-7 | 160.2 | Yes | Yes | Yes | | $IC_{50}$ = 3.2 nM for p38a MAP kinase.<br>$IC_{50}$ = 122 nM for p38b MAP kinase. | 14273220 | STE |

FIG. 1C

| | | | | | | | |
|---|---|---|---|---|---|---|---|
| p38 MAP Kinase Inhibitor VIII | 321351-00-2 | 415.7 | Yes | Yes | Yes | $IC_{50}$ = 40 nM for p38α. | 9801969 | STE |
| BIRB 796 | 285983-48-4 | 527.7 | Yes | Yes | Yes | $IC_{50}$ = 8 and 97 nM, respectively, against human p38α, with or without 2 h preincubation, but high affinity t1/2 of dissociation from human p38α = 23 h | 1384477 | STE |
| SB203580 | 152121-47-6 | 377.4 | Yes | Yes | Yes | $IC_{50}$ = 34 nM in vitro, 600 nM in cells for p38 MAPK | 176155 | STE |
| UCN-01 | 112953-11-4 | 482.5 | Yes | Yes | Yes | $IC_{50}$ = 29 nM for PKCα, $IC_{50}$ = 34 nM for PKCβ, $IC_{50}$ = 30 nM for PCKγ, $IC_{50}$ = 590 nM for PCKδ, $IC_{50}$ = 530 nM for PKCε. | 3072819 | AGC CAMK CMGC TK |
| Ro-31-8220 | 138489-18-6 | 553.7 | Yes | Yes | Yes | $IC_{50}$ = 10 nM for protein kinase C. | 14632205 | AGC CMGC |
| SB 203580, Sulfone | 152121-46-5 | 393.4 | Yes | Yes | Yes | $IC_{50}$ = 30 nM for p38 MAP kinase. $IC_{50}$ = 200 nM for inhibiting IL-1 production in human monocytes. | 5610352 | CMGC |
| SB 239063 | 193551-21-2 | 368.4 | Yes | Yes | Yes | $IC_{50}$ = 44 nM for MAP kinase p38a. $IC_{50}$ = 44 nM for MAP kinase p38b. $IC_{50}$ = 120 nM for IL-1, α. $IC_{50}$ = 350 nM for TNF-α. | 5186 | CMGC |

FIG. 2
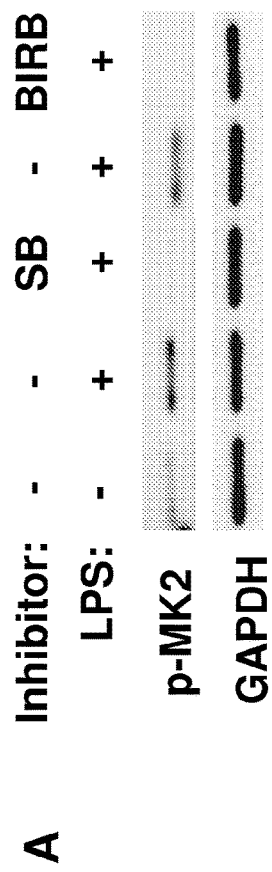
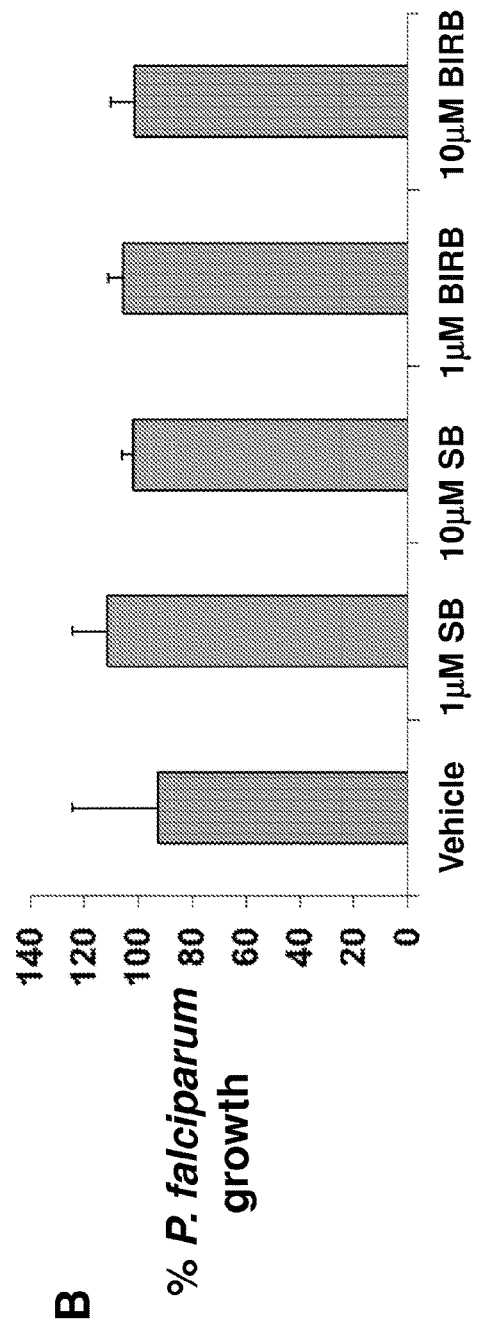

COMBINATION THERAPIES FOR MALARIA

CROSS-REFERENCE TO RELATED APPLICATIONS

This application is a U.S. National Phase patent application of PCT/US2014/046440, filed Jul. 11, 2014, which claims the benefit of U.S. Provisional Application No. 61/923,405, filed Jan. 3, 2014, and U.S. Provisional Application No. 61/845,920, filed Jul. 12, 2013, which are incorporated herein by reference in their entirety for all purposes.

STATEMENT REGARDING FEDERALLY SPONSORED RESEARCH OR DEVELOPMENT

This invention was made with Government support under Grant Nos. AI073745 and AI080799, awarded by the National Institutes of Health. The Government has certain rights in this invention.

FIELD

The present disclosure provides methods for treating or preventing malaria by administration of a protein kinase inhibitor and optionally one or both of a further protein kinase inhibitor and an antimalarial drug to a mammalian subject infected with or at risk of exposure to *Plasmodium* sp. In some aspects, the therapeutic and prophylactic regimens of the present disclosure are effective in reducing parasite development in mosquitoes feeding on recipients of the regimens, thereby reducing the risk of malaria transmission. Additionally, the present disclosure provides methods for screening candidate antimalarial agents.

BACKGROUND

Malaria is an infectious disease widespread in tropical and sub-tropical regions of Africa, Asia, and the Americas. In 2010 the World Health Organization estimated that there were over 219 million documented cases of malaria and between 660,000 and 1.2 million deaths from the disease (Nayyar, Lancet Infectious Diseases, 12:488-496, 2012). Malaria initially manifests with mild to severe symptoms including: chills, fever, fatigue, headache, and nausea. Later symptoms include severe anemia, and blood clotting, which can lead to brain damage and other complications, and death. Although five species of *Plasmodium* (*P. falciparum, P. vivax, P. ovale, P. malariae*, and *P. knowlesi*) can infect humans, the majority of malarial deaths are caused by *P. falciparum* and *P. vivax*.

*Plasmodium* parasites are transmitted to a human host primarily through a bite from an infected mosquito. The parasites are released into the blood stream of the human host from the salivary glands of the infected mosquito and travel to the liver. At this stage, the parasites are called sporozoites. The sporozoites asexually reproduce in the liver, a process called tissue schizogony, to produce genetically identical copies of the sporozoites, called merozoites. The merozoites leave the liver and infect red blood cells, where they undergo several rounds of asexual reproduction (blood schizogony) to produce new merozoites for continued red blood cell infection. Some merozoites mature into sexual stage gametocytes that are infective to mosquitoes. When a mosquito bites an infected person, ingested gametocytes enter the mosquito gut where they mature. Mature male and female gametes fuse in the gut of the mosquito to form zygotes, which ultimately develop into sporozoites.

Current strategies for treating malaria include the use of antimalarial drugs such as chloroquine and artemisinin. These drugs work by targeting the parasite and therefore, it is possible for parasites to develop resistance to current therapeutics. Widespread drug resistance in *Plasmodium* spp. has undermined the effectiveness of many of antimalarials used commonly, particularly chloroquine (Hyde, Trends Parasitol, 21:494-498, 2005). Combination therapy is required to combat these resistant strains and preserve antimalarial effectiveness. Artemisinin-derived drugs such as artesunate and artemether are effective against multi-drug resistant strains of *P. falciparum* (Alin and Bjorkman, Am J Trop Med Hyg, 50:771-776, 1994; van Vugt et al., Trans R Soc Trop Med Hyg, 94:545-548, 2000), and are highly potent against asexual forms, rapidly reducing parasitemia (Price et al., Trans R Soc Trop Med Hyg, 91:574-577, 1997; and Angus et al., Antimicrob Agents Chemother, 46:778-782, 2002). However, effective monotherapy requires seven days of treatment, increasing the risk of resistance development through poor compliance. Indeed, artemisinin-resistant malaria has already emerged (Fairhurst et al., Am J Trop Med Hyg, 87:231-241, 2012). For this reason, artemisinin-derived drugs must be combined with at least one other antimalarial. For example, the WHO Tropical Disease Research program, the Medicines for Malaria Venture (MMV), and GlaxoSmithKline formed a partnership to build upon a two-drug antimalarial including chlorproguanil and dapsone (Winstanley, Trop Med Int Health, 6:952-954, 2001) by adding artesunate to the combination.

The three-drug therapy including chlorproguanil, dapsone and artesunate is called CDA. Unfortunately, this therapy has negative side effects for some individuals who become infected with malaria parasites. The combination of chlorproguanil and dapsone can produce hemolysis, shorten red blood cell lifespan and induce methemoglobinemia, particularly in glucose-6-phosphate dehydrogenase (G6PD)-deficient individuals to the point that this combination was banned for malaria-infected individuals with this disorder. Due to this side effect, GlaxoSmithKline removed CDA from the market in 2008 (Luzzatto, Lancet, 376:739-741, 2010). The same side effects were observed during the use of CDA for treating uncomplicated malaria in G6PD-deficient children (Van Malderen et al., Malaria J, 11:139, 2012).

Therefore, there remains a need for an antimalarial therapy regimen that is essentially resistant to evasion by *Plasmodium* spp. In addition, there remains a need for antimalarials that are safe for use by G6PD-deficient individuals.

BRIEF SUMMARY

In one aspect, the present disclosure provides methods for treating or preventing malaria by administration of a protein kinase inhibitor and optionally one or both of a further protein kinase inhibitor and an antimalarial drug to a mammalian subject infected with or at risk of exposure to *Plasmodium* sp. In some aspects, the therapeutic and prophylactic regimens of the present disclosure are effective in reducing parasite development in mosquitoes feeding on recipients of the regimens. Additionally, the present disclosure provides methods for screening candidate antimalarial agents.

In particular, the present disclosure provides methods for treating or preventing malaria comprising: administering a protein kinase inhibitor to a mammalian subject in need thereof under conditions effective for treating or preventing malaria. In some embodiments, the present disclosure provides methods for treating or preventing malaria comprising: administering a first protein kinase inhibitor and a second protein kinase inhibitor to a mammalian subject in need thereof under conditions effective for treating or preventing malaria. In some embodiments, the first and second inhibitors are administered sequentially, while in other embodiments, the first and second inhibitors are administered concurrently. In some preferred embodiments, the administering reduces activity of a first mammalian protein kinase and a second mammalian protein kinase. In some embodiments, the first and second mammalian protein kinases comprise a member of one or more families selected from the group consisting of a protein kinase C (PKC) family, a c-Jun N-terminal kinase (JNK) family, and a p38 mitogen activated protein kinase (MAPK) family. In some embodiments, the first and second mammalian kinases are members of the PKC family and the MAPK family, respectively. In some preferred embodiments, one or both of the first and second kinase inhibitors reduce activity of a mosquito kinase. In some embodiments, the mosquito kinase comprises one or more of the group consisting of cPKC, nPKC-delta, nPKC-epsilon, aPKC-zeta, PKD, PKN, JNKa, JNKb and p38 MAPK. In some embodiments, the mosquito kinase comprises aPKC-zeta. In some embodiments, the subject is infected with *P. falciparum, P. vivax, P. ovale, P. malariae,* or *P. knowlesi*. In some embodiments, the subject is infected with a chloroquine-resistant *Plasmodium* sp. In some embodiments, the subject is experiencing one or both of chills and fever prior to the administering step. In some embodiments, treating malaria comprises alleviating a symptom of malaria experienced by the subject. In some embodiments, the methods further comprise administering an effective amount of an additional antimalarial drug to the mammalian subject. In some embodiments, the additional antimalarial drug comprises one or more compounds of the antimalarial classes selected from the group consisting of amino alcohols, aminoquinolines, antibiotics, antifolates, endoperoxides, sulfonamides, and others. In some embodiments, the subject is an uninfected individual planning to visit a malaria endemic area after (6 hours-72 hours, 1, to or 3 days) the administering step. That is the individual is not infected with but likely to be exposed to a *Plasmodium* sp. In some embodiments, the administering commences and concludes before the uninfected individual visits a malaria endemic area. In other embodiments, the administering commences before the uninfected individual visits a malaria endemic area, and continues during the duration of their visit. That is in some embodiments, the administering concludes some time after the uninfected individual leaves the malaria endemic area (e.g., within thirty days of after last potential exposure). In some embodiments, preventing malaria comprises protecting the subject from developing parasitemia during their visit to the malaria endemic area for a period of up to thirty days (between 0 and 30 days). In some embodiments, chloroquine-resistant *Plasmodium* sp. are known to be present in the malaria endemic area.

Additionally, the present disclosure provides methods for treating or preventing malaria comprising: administering a protein kinase inhibitor and an additional antimalarial drug to a mammalian subject in need thereof under conditions effective for treating or preventing malaria. In some embodiments, the protein kinase inhibitor and the additional antimalarial drug are administered sequentially, while in other embodiments the protein kinase inhibitor and the additional antimalarial drug are administered concurrently. In some embodiments, the protein kinase inhibitor comprises a first and a second protein kinase inhibitor. In some embodiments, the administering reduces activity of at least one mammalian protein kinase. In some embodiments, the mammalian protein kinase comprises a member of one or more families selected from the group consisting of a protein kinase C (PKC) family, a c-Jun N-terminal kinase (JNK) family, and a p38 mitogen activated protein kinase (MAPK) family. In some preferred embodiments, the protein kinase inhibitors reduce activity of a mosquito kinase. In some embodiments, the mosquito kinase comprises one or more of the group consisting of cPKC, nPKC-delta, nPKC-epsilon, aPKC-zeta, PKD, PKN, JNKa, JNKb and p38 MAPK. In some embodiments, the mosquito kinase comprises aPKC-zeta. In some embodiments, the subject is infected with *P. falciparum, P. vivax, P. ovale, P. malariae,* or *P. knowlesi*. In some embodiments, the subject is infected with a chloroquine-resistant *Plasmodium* sp. In some embodiments, the subject is experiencing one or both of chills and fever prior to the administering step. In some embodiments, treating malaria comprises alleviating a symptom of malaria experienced by the subject. In some embodiments, the additional antimalarial drug comprises one or more compounds of the antimalarial classes selected from the group consisting of amino alcohols, aminoquinolines, antibiotics, antifolates, endoperoxides, sulfonamides, and others. In some embodiments, the subject is an uninfected individual planning to visit a malaria endemic area after (6 hours-72 hours, 1, to or 3 days) the administering step. That is the individual is not infected with but likely to be exposed to a *Plasmodium* sp. In some embodiments, preventing malaria comprises protecting the subject from developing parasitemia during their visit to the malaria endemic area for a period of up to thirty days (between 0 and 30 days). In some embodiments, chloroquine-resistant *Plasmodium* sp. are known to be present in the malaria endemic area.

Furthermore, the present disclosure provides methods of reducing transmission of a *Plasmodium* sp. by a mosquito vector, comprising administering a protein kinase inhibitor to a mammalian subject infected with a *Plasmodium* sp. under conditions effective for reducing transmission of the *Plasmodium* sp. ingested by the mosquito vector in the subject's blood. The present disclosure also provides methods of reducing transmission of a *Plasmodium* sp. by a mosquito vector, comprising providing a bloodmeal comprising erythrocytes infected with a *Plasmodium* sp. to a mosquito vector in the presence of an effective amount of a protein kinase inhibitor for reducing transmission of the *Plasmodium* sp. ingested by the mosquito vector in the bloodmeal. In some embodiments, the methods further comprise administering an additional antimalarial drug to the mammalian subject. In some embodiments, the bloodmeal is provided to the mosquito vector in the further presence of an additional antimalarial drug. In some embodiments, the protein kinase inhibitor comprises a first and a second protein kinase inhibitor. In some embodiments, the protein kinase inhibitor reduces activity of at least one mammalian protein kinase. In some embodiments, the mammalian protein kinase comprises a member of one or more families selected from the group consisting of a protein kinase C (PKC) family, a c-Jun N-terminal kinase (JNK) family, and a p38 mitogen activated protein kinase (MAPK) family. In some preferred embodiments, the protein kinase inhibitor reduces activity of a mosquito kinase. In some embodiments, the mosquito kinase comprises one or more of the group consisting of cPKC, nPKC-delta, nPKC-epsilon, aPKC-zeta, PKD, PKN, JNKa, JNKb and p38 MAPK. In some embodiments, the mosquito kinase comprises aPKC-zeta. In some embodiments, the subject is infected with *P.*

*falciparum, P. vivax, P. ovale, P. malariae*, or *P. knowlesi*. In some embodiments, the subject is infected with a chloroquine-resistant *Plasmodium* sp. In some embodiments, the additional antimalarial drug comprises one or more compounds of the antimalarial classes selected from the group consisting of amino alcohols, aminoquinolines, antibiotics, antifolates, endoperoxides, sulfonamides, and others.

In addition, the present disclosure provides methods of identifying an antimalarial compound, comprising: measuring activity of a human or mosquito protein kinase in the presence and absence of a test compound; and identifying the test compound as an antimalarial compound when the activity of the protein kinase is reduced in the presence as compared to the absence of the test compound. In some embodiments, the methods further comprising growing mosquito cells in vitro in the presence and absence of the test compound and identifying the test compound as mosquito-cell safe when viability or doubling time of the mosquito cells is not significantly reduced in the presence as compared to the absence of the test compound. In some embodiments, the protein kinase is a human protein kinase. In some embodiments, the protein kinase is a mosquito protein kinase. In some embodiments, the human protein kinase comprises a member of one or more families selected from the group consisting of a protein kinase C (PKC) family, a c-Jun N-terminal kinase (JNK) family, and a p38 mitogen activated protein kinase (MAPK) family. In some embodiments, the mosquito kinase comprises one or more of the group consisting of cPKC, nPKC-delta, nPKC-epsilon, aPKC-zeta, PKD, PKN, JNKa, JNKb and p38 MAPK. In some embodiments, the mosquito kinase comprises aPKC-zeta. In some embodiments, the mosquito cells are *Anopheles stephensi* or *Anopheles gambiae* cells. The present disclosure also provides methods of identifying an antimalarial compound, comprising: comparing development of oocysts or sporozoites in mosquitoes after consumption of a bloodmeal comprising *Plasmodium* sp. in the presence and absence of a test compound; and identifying the test compound as an antimalarial compound when the development of oocysts or sporozoites is reduced in the mosquitoes in the presence as compared to the absence of the test compound. In some embodiments, the identifying step comprises enumerating oocysts per mosquito midgut. In some embodiments, the *Plasmodium* sp. is *P. falciparum* or *P. yoelii yoelii*. In some embodiments, the mosquitoes are of a species selected from the group consisting of *Anopheles (Cellia) aconitus* Dönitz 1902; *Anopheles (Nyssorhynchus) albimanus* Wiedemann, 1820; *Anopheles (Nyssorhynchus) albitarsis* species complex; *Anopheles (Cellia) annularis* van der Wulp, 1884; *Anopheles (Nyssorhynchus) aquasalis* Curry, 1932; *Anopheles (Cellia) arabiensis* Patton, 1905; *Anopheles (Anopheles) atroparvus* van Thiel, 1927; *Anopheles (Cellia) balabacensis* Baisas, 1936; *Anopheles (Anopheles) barbirostris* species complex; *Anopheles (Cellia) culicifacies* species complex; *Anopheles (Nyssorhynchus) darlingi* Root, 1926; *Anopheles (Cellia) dirus* species complex; *Anopheles (Cellia) farauti* species complex; *Anopheles (Cellia) flavirostris* (Ludlow, 1914); *Anopheles (Cellia) fluviatilis* species complex; *Anopheles (Anopheles) freeborni* Aitken, 1939; *Anopheles (Cellia) funestus* Giles, 1900; *Anopheles (Cellia) gambiae* Giles, 1902; *Anopheles (Cellia) koliensis* Owen, 1945; *Anopheles (Anopheles) labranchiae* Falleroni, 1926; *Anopheles (Anopheles) lesteri* Baisas & Hu, 1936 (formerly *An. anthropophagus* in China); *Anopheles (Cellia) leucosphyrus* and *Anopheles (Cellia) latens*; *Anopheles (Cellia) maculatus* Group; *Anopheles (Nyssorhynchus) marajoara* Galvão & Damasceno, 1942; *Anopheles (Cellia) melas* Theobald, 1903; *Anopheles (Cellia) merus* Donitz, 1902; *Anopheles (Anopheles) messeae* Falleroni, 1926; *Anopheles (Cellia) minimus* species complex; *Anopheles (Cellia) moucheti* Evans, 1925; *Anopheles (Cellia) nili* species complex; *Anopheles (Nyssorhynchus) nuneztovari* species complex; *Anopheles (Anopheles) pseudopunctipennis* species complex; *Anopheles (Cellia) punctulatus* species complex; *Anopheles (Anopheles) quadrimaculatus* Say, 1824; *Anopheles (Anopheles) sacharovi* Favre, 1903; *Anopheles (Cellia) sergentii* species complex; *Anopheles (Anopheles) sinensis* species complex; *Anopheles (Cellia) stephensi* Liston, 1901; *Anopheles (Cellia) subpictus* species complex; *Anopheles (Cellia) sundaicus* species complex; and *Anopheles (Cellia) superpictus* Grassi, 1899. In some embodiments, the mosquitoes are *Anopheles stephensi*.

The present disclosure also provides pharmaceutical compositions comprising a first protein kinase inhibitor, a second protein kinase inhibitor, and one or both of a pharmaceutically acceptable excipient and carrier, wherein the kinase inhibitors are present in amounts effective to treat or prevent malaria in a mammalian subject. In some embodiments, the present disclosure provides pharmaceutical compositions comprising a protein kinase inhibitor, an additional antimalarial agent, and one or both of a pharmaceutically acceptable excipient and carrier, wherein the kinase inhibitor and the additional antimalarial agent are present in amounts effective to treat or prevent malaria in a mammalian subject. In some embodiments, the present disclosure provides pharmaceutical compositions comprising: a protein kinase inhibitor attached to a mitochondrial-targeting moiety, and one or both of a pharmaceutically acceptable excipient and carrier, wherein the protein kinase inhibitor is present in an amount effective to treat or prevent malaria in a mammalian subject.

BRIEF DESCRIPTION OF THE DRAWINGS

FIG. 1A-C provides names and structures of exemplary protein kinase inhibitors.

FIG. 2A-2B shows that *Anopheles stephensi* p38 MAPK can be inhibited by SB203580 (SB) and BIRB 796, although neither inhibitor directly altered *Plasmodium falciparum* growth in vitro. In FIG. 2A, *Anopheles stephensi* ASE cells were pre-incubated with 10 µM SB203580 or 10 µM BIRB 796 and 2 h later stimulated with 1 µg/ml LPS. Phosphorylation of MK2, a downstream protein kinase substrate activated by p38 MAPK, was analyzed by western blot. Vehicle treatment was used as control group. Note that p-MK2 levels are undetectable in cells pre-treated with either inhibitor. In FIG. 2B, in vitro culture of *P. falciparum* was synchronized, treated with 1 µM or 10 µM SB203580 or 1 µM or 10 µM BIRB 796 for 48 h, then fixed and stained with propidium iodide. Parasitemia was determined by flow cytometry. Data were analyzed by Student's t-test (alpha=0.05) and are represented as mean±SEM, n=3. Neither inhibitor significantly altered parasite growth relative to the vehicle control.

DETAILED DESCRIPTION

Figure 3:
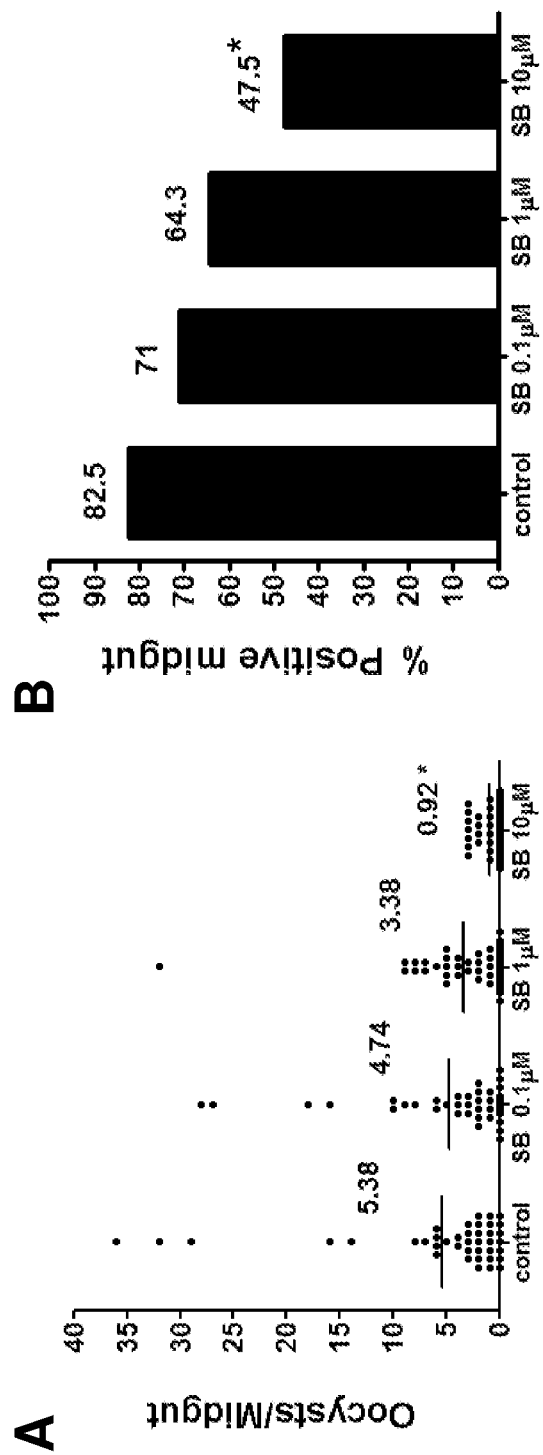
FIG. 3A-3D shows that inhibition of p38 MAPK signaling reduced *Plasmodium falciparum* development in *Anopheles stephensi*. Briefly, 3-5 d old female *A. stephensi* were fed a bloodmeal with *P. falciparum* supplemented with SB203580, BIRB 796, or diluent control. Midguts were dissected and oocysts were counted at 10 days following infection. Dots in FIG. 3A and FIG. 3C represent oocyst numbers in one midgut, while percentage positive midguts or percentage of midguts with at least one oocyst are represented as means in FIG. 3B and FIG. 3D. Mean oocysts per midgut (lines, numbers on graph) were analyzed by ANOVA (alpha=0.05) for overall significance and by Student-Neuman-Keuls for pairwise comparisons using Graphpad Prism version 4.0 (San Diego, Calif.). Prevalences of mosquito infection (indicated on graph) were analyzed by chi-square (alpha=0.05). At 10 μM, SB203580 significantly reduced *P. falciparum* oocysts/midgut and infection prevalence in *A. stephensi* (*).
Figure 3:
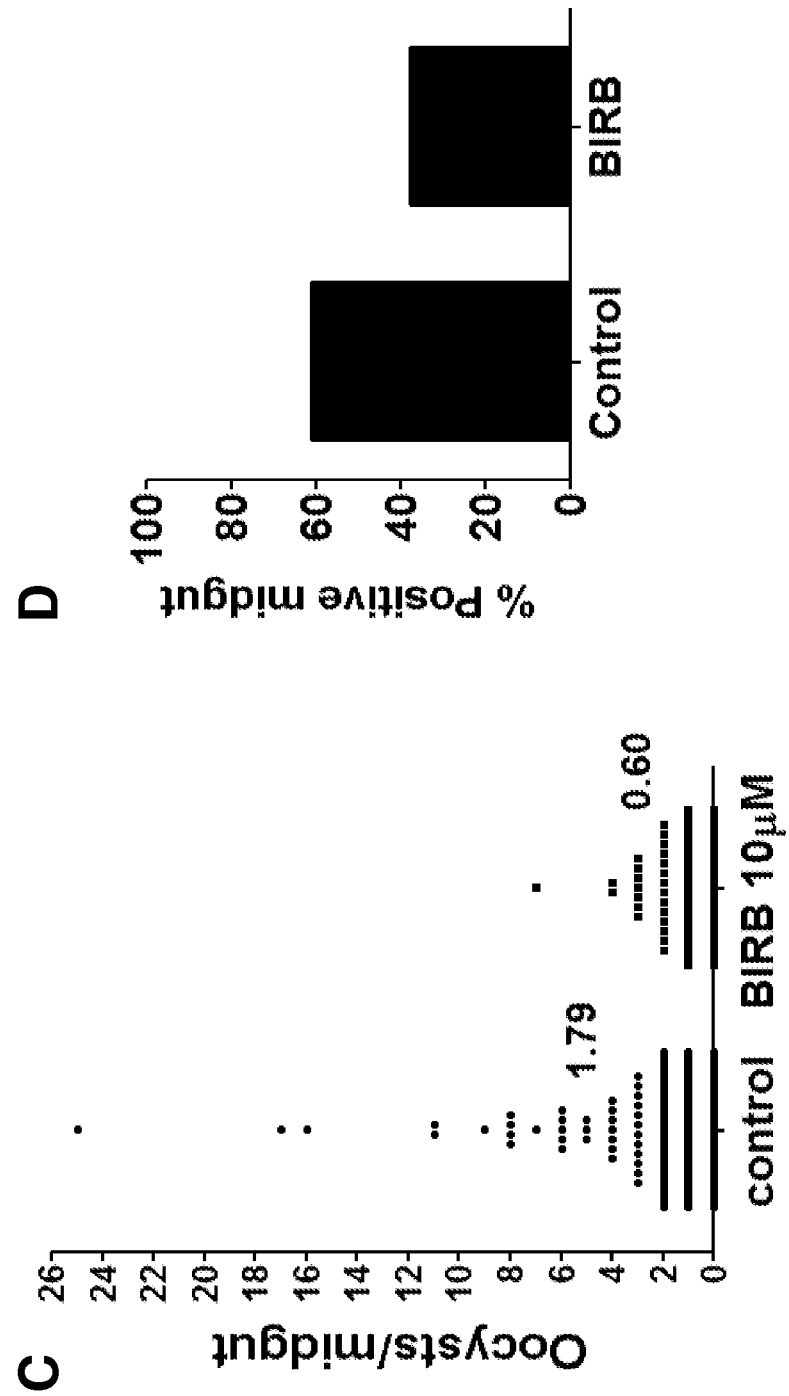
Figure 4:
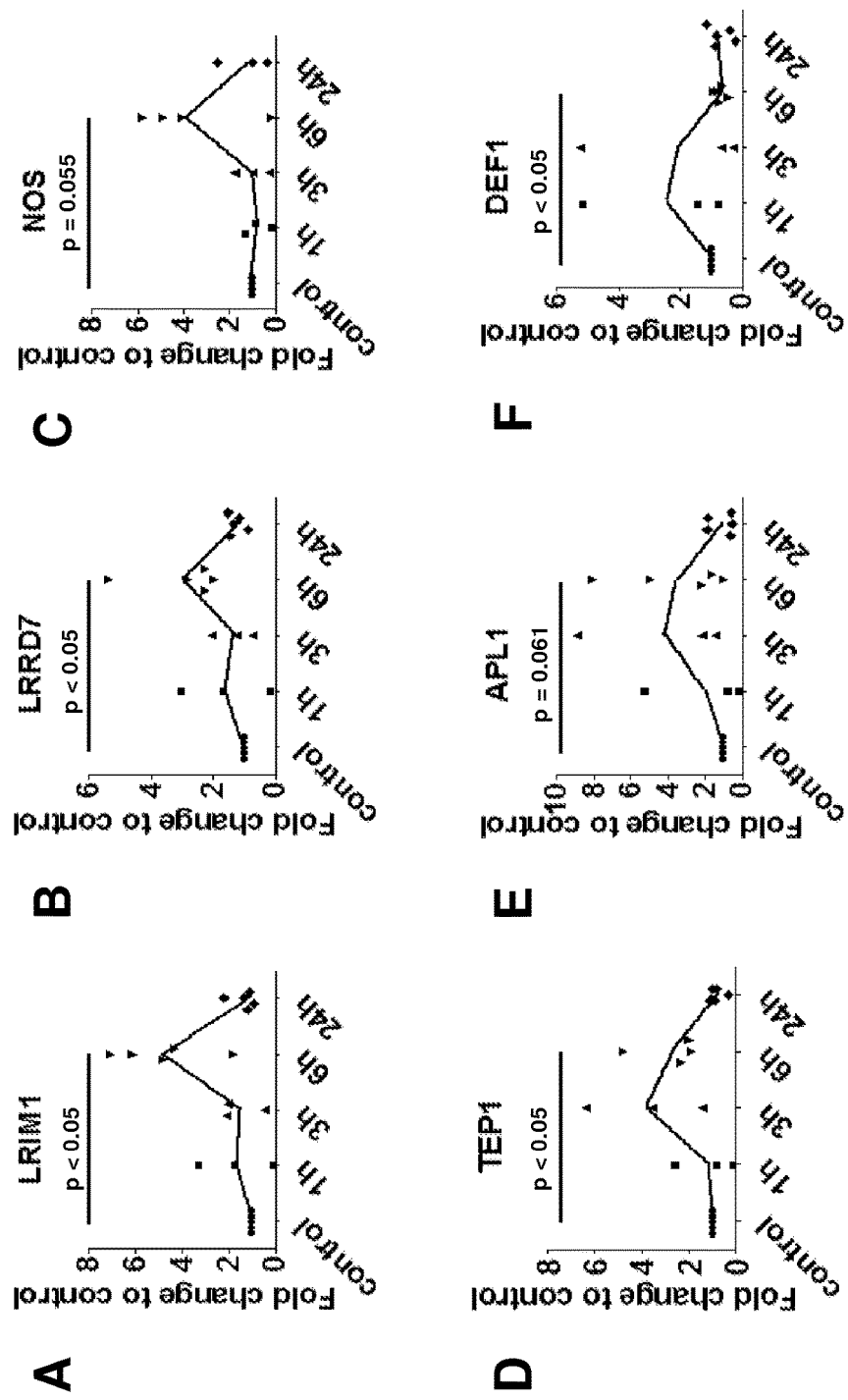
FIG. 4A-F shows that inhibition of *Anopheles stephensi* p38 MAPK in vivo increased midgut expression of anti-parasite genes. Briefly, 3-5 d old female *A. stephensi* were fed with killed lysate of *P. falciparum* supplemented with BIRB 796 or vehicle. Midgut samples were collected at 1-24 h post-feeding. Expression levels of anti-malarial genes at each time point were analyzed with quantitative PCR relative to the corresponding control group. Each dot represents the fold change in one repeat relative to control levels. Data were analyzed by Student's t-test (alpha=0.05), n=3-5. At 6 h post-feeding immune gene expression levels were significantly different from controls.

In one aspect, the present disclosure provides methods for treating or preventing malaria by administration of a protein kinase inhibitor and optionally one or both of a further protein kinase inhibitor and an antimalarial drug to a mammalian subject infected with or at risk of exposure to *Plasmodium* sp. In some aspects, the therapeutic and prophylactic regimens of the present disclosure are effective in reducing parasite development in mosquitoes feeding on recipients of the regimens. Additionally, the present disclosure provides methods for screening candidate antimalarial agents.

Kinase Inhibitors

PKC (protein kinase C) isoenzymes are an important family of serine/threonine protein kinases that contribute to many diverse cellular and tissue functions, as well as human disease pathologies including cancer development and progression (Bosco et al., Mini Rev Med Chem, 11:185-199, 2011; and Rosse et al., Nat Rev Mol Cell Biol, 11:103-112, 2010). The molecular architecture of PKC family members is conserved throughout the cPKC (classical PKC; cPKC α, cPKC β and cPKC γ), nPKC (novel PKC; nPKC δ, nPKC ε, nPKC η and nPKC θ) and aPKC (atypical PKC; a PKC ζ and aPKC τ) isoforms. All PKCs are comprised of a C-terminal serine/threonine protein kinase domain belonging to the AGC kinase (protein kinase A/protein kinase G/PKC family kinase) superfamily, and an N-terminal regulatory domain (Parker and Murray-Rust, J Cell Science, 117:131-132, 2004). The kinase domain has a C-terminal extension unique to AGC kinases that contains essential 'priming' phosphorylation sites required for catalytic activation (Pearce et al., Nat Rev Mol Cell Biol, 11:9-22, 2010), whereas in aPKCs, the most C-terminal of these is replaced by a phospho-mimetic Glu residue. The regulatory domain within all PKC isoforms has an inhibitory region (pseudo-substrate motif) and distinctive arrangements of C1, C2 and/or PB1 (Phox/Bem1) domains (the last being exclusive to the aPKCs) that together are crucial for conferring isoform-specific functions.

The aPKC isoforms (PKC ζ and PKC τ) diverge from other PKC family members as their regulatory domains are unresponsive to diacylglycerol, phosphatidylserine and $Ca^{2+}$. Instead they are regulated by protein interactions, for example with polarity proteins Par-6, Par-3 and the Rho family GTPase cdc42 (Suzuki and Ohno, J Cell Sci, 119: 979-987, 2003). aPKC has a role in establishing cell polarity and is required for normal cell proliferation, mitotic spindle orientation and migration.

There has been considerable interest in aPKCs as drug targets due to their roles in cancer development and progression (Fields and Regala, Pharmacol Res, 55:487-497, 2007). For example, PKC ζ is required for epidermal growth factor-induced migration of human breast and lung cancer cells and for colony-stimulating factor 1 chemotaxis of macrophages, among others. PKC τ promotes nicotine-induced migration and invasion of lung cancer cells via phosphorylation of calpains and is involved in other types of cancer. In addition, aPKC has been shown to interact with bona fide oncogenes, such as Ras and Notch in the fruit fly *Drosophila melanogaster* to promote an epithelial cell overgrowth that resembles cancer. Recent advances in malaria drug discovery have led to a proposal to use *Plasmodium* kinases as targets for next generation antimalarials (Zhang et al., Curr Top Med Chem, 12:456-472, 2012; Lin et al., PLoS One, 7, e49040, 2012; Lucet et al., Future Med Chem, 4:2295-2310, 2012; Aaberg et al., Biol Chem, 393:1121-1129, 2012; Biamonte at al., Bioorg Med Chem Lett, 23:2829-2843, 2013; Nag et al., Curr Drug Discovery Technol, 10:85-91, 2013; and Ochocki and Distefano, Med Chem Comm, 4:476-492, 2009). These reports, however, failed to consider manipulating kinase signalling pathways in the human or mosquito hosts to reduce parasitemia and block transmission.

Like many protein kinases, aPKC isoenzymes can be inhibited by small-molecule chemicals either through their ATP-binding or allosteric pockets (Knight and Shokat, Chem Biol, 12:621-637, 2005). Only a few selective chemical biology tools inhibit aPKC catalytic activity. These few catalytic inhibitors include the non-selective Gö6983 and Gö6976 compounds and a PKC ζ pseudo-substrate peptide containing a membrane-targeting myristoylation site (Roffey et al., Curr Opin Cell Biol, 21:268-279, 2009). The development of effective ATP-competitive inhibitors against aPKCs, similar to other protein kinases, has been complicated by challenges with both potency and selectivity. In general, such inhibitors acquire selectivity by associating with both the ATP-binding site and with adjacent residues, which are less well conserved. Other approaches include screening for allosteric inhibitors of PKC ζ that target the PIF pocket (Frohner et al., J Med Chem, 54:6714-6723, 2011; and Lopez-Garcia et al., Chem Biol, 18:1463-1473, 2011) or that block PKC τ. interaction with Par-6 (Pillai et al., Int J Biochem Cell Biol, 43:784-794, 2011; Erdogran et al., J Biol Chem, 281:28450-18459, 2006; and Regala et al., Cancer Res, 68: 5888-5895, 2008). Recent studies have shown differential effects between PKC ζ and PKC τ. for compounds targeting other aPKC-specific pockets outside of the ATP cleft. For instance, the use of CRT0066854 and its derivative compounds are predicted to be useful tools in further differentiating the roles of PKC ζ and PKC τ. in establishing cell polarity and growth-factor-stimulated signaling pathways (Kjaer et al., Biochem J, 451:329-342, 2013).

PKC ζ plays an important role in the activation of TNF-alpha and NF-kB pathways, the latter of which are critical to the balance between host protection and pathology in malaria (Randall and Engwerda, Exp Parasitol, 126:326-331, 2010). In the context of malaria parasite biology, mammalian PKC activity has recently been shown to be critical for malaria parasite egress from infected red blood cells (Millholland et al., Cell Host Microbe, 13:15-28, 2013). Intriguingly, erythrocyte PKCs are comprised of cPKCα, as well as aPKC ζ and aPKC τ. (Govekar and Zingde, Ann Hematol, 80:531-534, 2001). Thus during development of the present disclosure, aPKCs have been determined to be a primary target of PKC inhibitors that can reduce parasitemia. The effect on host RBC PKC activity is further substantiated by an examination of host versus parasite $IC_{50}$s (concentration required for 50% inhibition): the $IC_{50}$ for PKC ζ is 60 nM (Gschwendt et al., FEBS Lett, 392:77-80, 1996), whereas the $IC_{50}$ for the distantly (and only) related malaria parasite kinase PfPKB is >1000 nM (Kumar et al., J Biol Chem, 279:24255-24264, 2004). In the mosquito host, conserved PKC activity also controls parasite development: ingestion of PKC inhibitors, at levels consistent with those achievable in human blood, during feeding on an infected meal resulted in significantly reduced P. falciparum development in the mosquito Anopheles stephensi (Pakpour et al., PLoS One, 8(10): e76535). Further, expression of A. stephensi PKC mRNA was significantly increased (5-fold) in the mosquito midgut upon blood feeding, a change that was consistent with PKC-dependent regulation of epithelial barrier permeability that likely controls resistance to parasite infection.

Effective inhibitor targeting of PKC activity in general and for aPKCs in particular is challenging. However, networked kinases, which interact as kinase and kinase substrate, may provide an opportunity for novel inhibitor design. In the mosquito, p38 MAPK inhibition significantly reduces malaria parasite development, observations confirmed with commercially available p38 MAPK inhibitors during development of the present disclosure (FIG. 3A-D). Prior to this work, the p38 MAPK inhibitor SB203580 was reported to reduce P. falciparum replication in human erythrocytes in vitro at concentrations exceeding 5 µM (Brumlik et al., Exp Parasitol, 128:170-175, 2011). However, no such effects of SB203580 up to 10 µM and no activity of a second p38 MAPK inhibitor BIRB 796 up to 10 µM against P. falciparum growth in vitro was observed (FIG. 2B). However, both inhibitors at 10 µM significantly reduced p38 MAPK activity in the mosquito in vivo when provided in the bloodmeal immediately prior to feeding, indicating that mosquito p38 MAPK activity controls parasite development (FIG. 2A). In mammalian cells, the PKC ζ regulatory domain interacts directly with p38 MAPK kinase, which blocks PKC ζ activity by preventing its autophosphorylation on T560 (but not on S113 or S186) and activation (Kim et al., Cell Death Differ, 12:201-212, 2005). Thus strategies to target p38 MAPK can be leveraged to enhance aPKC targeting. Specifically, in some embodiments, a PKC inhibitor (e.g., a molecule that is directed to the PKC ζ PIF pocket) is used in combination with a p38 MAPK inhibitor to inhibit networked p38 MAPK and PKC ζ to enhance control of infection in the human host and transmission via the exposed mosquito. Of note, some p38 MAPK inhibitors have progressed into human clinical trials for not only cancer but also to inflammatory disease and cardiovascular disease with manageable side effects (Hammaker et al., Ann Rheum Dis, 69(S1):77-82, 2010).

In addition to inhibitors of aPKC and p38 MAPK, other kinase inhibitors, such as the JNK inhibitor SP600125 has been shown to reduce malaria disease severity, but without an effect on parasitemia (Anand et al., Parasitol Res, 112:1959-1966, 2013). However, during development of the present disclosure, inhibition of mosquito JNK activity was found to alter P. falciparum development in A. stephensi. Hence, in some embodiments, a JNK inhibitor in combination with a PKC inhibitor is used to reduce disease severity and parasitemia. Combinations of small molecule inhibitors (SMIs) of conserved kinases are provided as "next-generation" anti-malarials to control both disease severity and transmission, as well as to reduce risk of development of parasite drug resistance.

In some embodiments, SMIs of conserved signaling kinases are delivered as orally available therapeutics to malaria patients in endemic countries. The following list of SMI therapeutic attributes is applicable to both pediatric and adult patients: (1) single dose (or few dose) efficacy with inhibition of parasite growth and resolution of disease following treatment, (2) few to no contraindications and side effects, (3) long-term stability under conditions in endemic countries where refrigeration during storage and distribution are limited at best, (4) parasite transmission blocking activity in mosquitoes that feed on treated patients to counter potential "escape" of parasites from treated patients, (5) well-tolerated by the most sensitive populations, children and pregnant women as well as by G6PD-deficient patients.

Structures of exemplary kinase inhibitors are shown in FIG. 1. Kinase inhibitors for use in the methods of the present disclosure include but are not limited to inhibitors of PKC, JNK, MAPK and other kinases, as well as salts and derivatives thereof. Exemplary PKC inhibitors include: bisindolylmaleimide IV (3,4-bis(1H-indol-3-yl)pyrrole-2,5-dione); chelerythrine chloride (1,2-dimethoxy-12-methyl-[1,3]benzodioxolo[5,6-c]phenanthridin-12-ium; chloride); Go 6976 (5,6,7,13-Tetrahydro-13-methyl-5-oxo--12H-indolo[2,3-a]pyrrolo[3,4-c]carbazole-12-propa-nenitrile); Go 6983 (3-[1-[3-(dimethylamino)propyl]-5-methoxyindol-3-yl]-4-(1H-indol-3-yl)pyrrole-2,5-dione); PKCβII/EGFR Inhibitor (5,6-bis(4-fluoroanilino)isoindole-1,3-dione); PKCβ Inhibitor (3-anilino-4-[1-(3-imidazol-1-ylpropyl)indol-3-yl]pyrrole-2,5-dione); N-benzoyl-staurosporine, staurosporine (Streptomyces sp.); bisindolylmaleimide III, hydrochloride (3-[1-(3-aminopropyl)indol-3-yl]-4-(1H-indol-3-yl)pyrrole-2, 5-dione; hydrochloride); Go 7874, hydrochloride; H-8, dihydrochloride (N-[2-(methylamino)ethyl]isoquinoline-5-sulfonamide; dihydrochloride); HA 1004, dihydrochloride (2-[2-(isoquinolin-5-ylsulfonylamino)ethyl]guanidine; dihydrochloride); UCN-01 (7-hydroxystaurosporine); and Ro-31-8220 (methanesulfonic acid; 3-[3-[4-(1-methylindol-3-yl)-2,5-dioxopyrrol-3-yl]indol-1-yl]propyl carbamimidothioate). Exemplary MAPK inhibitors include: p38 MAP Kinase Inhibitor IV (3,4,6-trichloro-2-(2,3,5-trichloro-6-hydroxyphenyl)sulfonylphenol); p38 MAP Kinase Inhibitor VI, JX401 ((4-benzylpiperidin-1-yl)-(2-methoxy-4-methylsulfanylphenyl)methanone); p38 MAP Kinase Inhibitor VII, SD-169 (1H-indole-5-carboxamide); p38 MAP Kinase Inhibitor VIII ([4-(2-amino-4-bromoanilino)-2-chlorophenyl]-(2-methylphenyl)methanone); BIRB 796 (1-[5-tert-butyl-2-(4-methylphenyl)pyrazol-3-yl]-3-[4-(2-morpholin-4- ylethoxy)naphthalen-1-yl]urea); SB203580 (4-[4-(4-fluorophenyl)-2-(4-methylsulfinylphenyl)-1H-imidazol-5-yl]pyridine); SB 203580, Sulfone (4-[4-(4-fluorophenyl)-2-(4-methylsulfonylphenyl)-1H-imidazol-5-yl]pyridine); and SB 239063 (4-[4-(4-fluorophenyl)-5-(2-methoxypyrimidin-4-yl)imidazol-1-yl]cyclohexan-1-ol). Exemplary inhibitors of other kinases include: U0126 ((2Z,3Z)-2,3-bis[amino-(2-aminophenyl)sulfanylmethylidene]butanedinitrile); PD98059 (2-(2-amino-3-methoxyphenyl)chromen-4-one); and MEK1/2 Inhibitor II (N-(cyclopropylmethoxy)-3,4,5-trifluoro-2-(4-iodo-2-methylanilino)benzamide).

Additional kinase inhibitors for use in the methods and compositions of the present disclosure are listed in Tables I-IV below.

TABLE I

Exemplary PKCepsilon Inhibitors

| Description | CAS No. | PubChem CID | Parameter (nM) |
|---|---|---|---|
| Staurosporine | 62996-74-1 | 5279 | $IC_{50} = 0.08$ |
| Phorbol 12,13-dibutyrate | 37558-16-0 | 37783 | $Kd = 0.81$ |
| SureCN2934634 | N/A | 45375865 | $IC_{50} = 1.6$ |
| GSK690693 | 937174-76-0 | 16725726 | $Kd = 5.3$ |
| Sotrastaurin | 425637-18-9 | 10296883 | $IC_{50} = 6.2$ |
| Indolactam V | 90365-57-4 | 105000 | $Ki = 7.7$ |
| Enzastaurin | 170364-57-5 | 176167 | $Kd = 8.9$ |
| CHEMBL350335 | N/A | 9847089 | $IC_{50} = 10$ |
| Balanol analog 4 | N/A | 5327921 | $IC_{50} = 10$ |
| Ro-31-8220 | 138489-18-6 | 5083 | $IC_{50} = 10$ |
| Ruboxistaurin | 169939-94-0 | 153999 | $Kd = 11$ |
| A674563 | 552325-73-2 | 11314340 | $Kd = 11$ |
| CHEMBL606245 | N/A | 44160269 | $IC_{50} = 14$ |
| Ro-32-0432 | 151342-35-7 | 127757 | $IC_{50} = 17.2$ |
| Ophiocordin | 63590-19-2 | 5287736 | $IC_{50} = 20$ |
| Cediranib | 288383-20-0 | 9933475 | $IC_{50} = 24$ |
| Bisindolylmaleimide I | 133052-90-1 | 2396 | $IC_{50} < 25$ |
| K-252a | 97161-97-2 | 3813 | $IC_{50} = 33$ |
| SureCN2934911 | N/A | 45375866 | $IC_{50} = 36$ |
| Ro-32-0557 | N/A | 19095896 | $IC_{50} = 48$ |
| PKCb Inhibitor | 257879-35-9 | 6419755 | $IC_{50} > 50$ |
| Cdk1/2 Inhibitor III | 443798-55-8 | 5330812 | $IC_{50} > 50$ |
| N-Benzoylstaurosporine | 120685-11-2 | 56603681 | $IC_{50} = 50$ |
| Balanol analog 5 | N/A | 5327922 | $IC_{50} = 50$ |
| CHEMBL103055 | N/A | 10207821 | $IC_{50} = 75$ |
| AT9283 | 1092788-83-4 | 24905142 | $IC_{50} > 100$ |
| Bisindolylmaleimide XI, HCl | N/A | 11605552 | $IC_{50} = 108$ |
| CHEMBL295806 | N/A | 44294447 | $IC_{50} = 120$ |
| SureCN5757856 | N/A | 10302405 | $IC_{50} = 140$ |
| SB218078 | 135897-06-2 | 447446 | $IC_{50} > 150$ |
| PKR Inhibitor | 608512-97-6 | 6490494 | $IC_{50} > 150$ |
| Gö6983 | 133053-19-7 | 3499 | $IC_{50} > 150$ |
| Lestaurtinib | 111358-88-4 | 126565 | $Kd = 160$ |
| Bisindolylmaleimide IV | 119139-23-0 | 2399 | $IC_{50} = 190$ |
| Y-27632 | 146986-50-7 | 448042 | $IC_{50} > 250$ |
| Arcyriaflavin A | 118458-54-1 | 5327723 | $IC_{50} = 310$ |
| SureCN3774124 | N/A | 10209082 | $IC_{50} = 330$ |
| Alvocidib | 131740-09-5 | 9910986 | $Kd = 380$ |
| BMS-690514 | 859853-30-8 | 11349170 | $Kd < 400$ |
| BCP9000906 | 457081-03-7 | 5494425 | $IC_{50} = 500$ |
| H-1152; Glycyl | 913844-45-8 | 16760635 | $IC_{50} = 500$ |
| Ruxolitinib | 941678-49-5 | 25126798 | $Kd = 530$ |
| SureCN2579964 | N/A | 24948986 | $IC_{50} < 750$ |
| PP121 | 1092788-83-4 | 24905142 | $IC_{50} < 750$ |
| SureCN2505235 | N/A | 5353854 | $IC_{50} = 1000$ |
| WZ3146 | 1214265-56-1 | 44607360 | $Kd > 1000$ |
| WZ4002 | 213269-23-8 | 44607530 | $Kd > 1000$ |
| Icotinib | 610798-31-7 | 22024915 | $IC_{50} > 1000$ |
| MK5108 | 1010085-13-8 | 24748204 | $IC_{50} > 1000$ |
| JAK3 Inhibitor VI | 856436-16-3 | 16760524 | $IC_{50} > 1000$ |

TABLE II

Exemplary MAPK14 p38 Inhibitors

| Description | CAS No. | PubChem CID | Parameter (nM) |
|---|---|---|---|
| Doramapimod | 285983-48-4 | 156422 | $Kd = 0.046$ |
| SPDD01923 | N/A | 447721 | $IC_{50} = 0.11$ |
| Kinome_3519 | N/A | 16730109 | $Ki = 0.2$ |
| SCIO-469 | 309913-83-5 | 9871074 | $Kd = 0.48$ |
| VX745 | 209410-46-8 | 3038525 | $IC_{50} = 0.8$ |
| CHEMBL420047 | N/A | 23646852 | $Kd = 1$ |
| CHEMBL383172 | N/A | 11235063 | $Ki = 1.6$ |
| SureCN4219451 | N/A | 9999342 | $IC_{50} = 1.8$ |
| SureCN5632345 | N/A | 44593646 | $Ki = 1.9$ |
| PH797804 | 586379-66-0 | 22049997 | $IC_{50} = 2.5$ |
| CHEMBL215652 | N/A | 23647319 | $IC_{50} = 2.5$ |
| AMG-47a | 882663-88-9 | 16086114 | $IC_{50} = 3$ |
| SureCN4762364 | N/A | 10473563 | $IC_{50} = 3.2$ |
| VX702 | 745833-23-2 | 10341154 | $Kd = 3.7$ |
| SureCN3936664 | N/A | 11626920 | $IC_{50} = 5$ |
| Aminopyrimidine amide, 13b | N/A | 16118737 | $IC_{50} = 5$ |
| 2ofv | N/A | 15991573 | $IC_{50} = 6$ |
| LY2228820 | 862507-23-1 | 11570805 | $IC_{50} = 7$ |
| CHEMBL213451 | N/A | 23647330 | $IC_{50} = 7.6$ |
| SureCN5495613 | 913376-83-7 | 24764449 | $IC_{50} = 9$ |
| SureCN6744546 | N/A | 24856363 | $Ki = 9$ |
| SureCN5774497 | N/A | 9948405 | $IC_{50} = 9.6$ |
| SB202190 | 152121-30-7 | 5353940 | $Kd = 9.8$ |
| SB203580 | 152121-47-6 | 176155 | $IC_{50} = 10$ |
| CHEMBL1964275 | N/A | 57394915 | $Kd < 10$ |
| SB220025 | 165806-53-1 | 5164 | $IC_{50} = 19$ |
| Dasatinib | 302962-49-8 | 11153014 | $Kd = 27$ |
| p38 MAP Kinase Inhibitor | 219138-24-6 | 4665 | $IC_{50} = 35$ |
| Sorafenib | 284461-73-0 | 216239 | $IC_{50} = 38$ |
| CHEMBL1092754 | N/A | 44541014 | $IC_{50} = 50$ |
| PD169316 | 152121-53-4 | 4712 | $IC_{50} > 50$ |
| AST-487 | 630124-46-8 | 11409972 | $Kd = 73$ |
| A-83-01 | 909910-43-6 | 16218924 | $IC_{50} < 100$ |
| SB681323 | 444606-18-2 | 10297982 | $IC_{50} < 100$ |
| AT9283 | 1092788-83-4 | 24905142 | $IC_{50} > 100$ |
| Regorafenib | 755037-03-7 | 11167602 | $IC_{50} < 100$ |
| 7-hydroxystaurosporine | 112953-11-4 | 72271 | $IC_{50} = 100$ |
| SKF-86002 | 72873-74-6 | 5228 | $IC_{50} = 110$ |
| Nilotinib | 641571-10-0 | 644241 | $IC_{50} > 150$ |
| ZM336372 | 208260-29-1 | 5730 | $IC_{50} = 180$ |
| CHEMBL364623 | 302962-49-8 | 11153014 | $IC_{50} = 202$ |
| FR180204 | 865362-74-9 | 11493598 | $Ki = 310$ |
| Foretinib | 849217-64-7 | 42642645 | $Kd = 320$ |
| ML3403 | 581098-48-8 | 6419739 | $IC_{50} = 380$ |
| SureCN4875304 | N/A | 46871765 | $IC_{50} = 540$ |
| AG1478 | 175178-82-2 | 2051 | $IC_{50} = 560$ |
| HG-9-91-01 | N/A | N/A | $IC_{50} < 600$ |
| LY364947 | 396129-53-6 | 447966 | $IC_{50} = 740$ |
| Celocoxib | 194044-54-7 | 2662 | $IC_{50} = 810$ |
| BX517 | N/A | 11161844 | $IC_{50} > 900$ |

TABLE III

Exemplary JNK1 Inhibitors

| Description | CAS No. | PubChem CID | Parameter (nM) |
|---|---|---|---|
| Kinome_3027 | N/A | 11640926 | $Ki = 1$ nM |
| JNK Inhibitor VIII | 894804-07-0 | 11624601 | $Ki = 2$ nM |
| Kinome_3024 | N/A | 11539329 | $Ki = 3$ nM |
| Kinome_3028 | N/A | 11590363 | $Ki = 3$ nM |
| Kinome_2553 | N/A | 16007116 | $Ki = 3.8$ nM |
| Hesperadin | 422513-13-1 | 10142586 | $Kd < 10$ nM |
| Lestaurtinib | 111358-88-4 | 126565 | $Kd = 11$ nM |
| R406 | 841290-81-1 | 11984591 | $Kd = 38$ |
| JNKIN7 | N/A | 57340685 | $IC_{50} < 40$ nM |
| JNKIN8 | N/A | 57340686 | $IC_{50} < 40$ nM |
| TTT-3002 | N/A | N/A | $IC_{50} < 40$ nM |
| 1;9-Pyrazoloanthrone | 129-56-6 | 8515 | $IC_{50} = 40$ nM |
| 7-hydroxystaurosporine | 112953-11-4 | 72271 | $IC_{50} < 45$ nM |
| Momelotinib | 1056634-68-4 | 25062766 | $IC_{50} < 100$ nM |

TABLE III-continued

Exemplary JNK1 Inhibitors

| Description | CAS No. | PubChem CID | Parameter (nM) |
|---|---|---|---|
| Gö6976 | 136194-77-9 | 3501 | $IC_{50} = 100$ nM |
| AT9283 | 1092788-83-4 | 24905142 | $IC_{50} > 100$ nM |
| Staurosporine aglycone | 99533-80-9 | 3035817 | $IC_{50} < 100$ nM |
| PP1 Analog II; 1NM-PP1 | 221244-14-0 | 5154691 | $IC_{50} = 140$ nM |
| K-252a | 97161-97-2 | 3813 | $IC_{50} > 150$ nM |
| AS601245 | 345987-15-7 | 11422035 | $IC_{50} = 150$ nM |
| CHEMBL1788116 | N/A | 11422034 | $IC_{50} = 150$ nM |
| NVP-TAE684 | 761439-42-3 | 16038120 | $Kd = 160$ nM |
| GSK1838705A | 1116235-97-2 | 25182616 | $Kd = 210$ nM |
| Staurosporine | 62996-74-1 | 5279 | $Kd = 220$ nM |
| TG101348 | 936091-26-8 | 16722836 | $Kd = 260$ nM |
| Nilotinib | 641571-10-0 | 644241 | $Kd = 450$ nM |
| AST-487 | 630124-46-8 | 11409972 | $Kd = 460$ nM |
| NU6140 | 444723-13-1 | 10202471 | $IC_{50} = 500$ nM |
| KW2449 | 1000669-72-6 | 11427553 | $Kd = 580$ nM |
| CZC-25146 | 330003-04-7 | N/A | $IC_{50} < 600$ nM |
| Nintedanib | 928326-83-4 | 9809715 | $Kd = 630$ nM |
| KT5720 | 108068-98-0 | 3844 | $IC_{50} < 800$ nM |
| BX517 | N/A | 11161844 | $IC_{50} > 900$ nM |
| A 443654 | 552325-16-3 | 10172943 | $IC_{50} > 900$ nM |
| Pyrrolo-pyrimidone; 17 | N/A | 16119021 | $IC_{50} = 960$ nM |
| WZ3146 | 1214265-56-1 | 44607360 | $Kd > 1000$ nM |
| WZ4002 | 213269-23-8 | 44607530 | $Kd > 1000$ nM |
| MK5108 | 1010085-13-8 | 24748204 | $IC_{50} > 1000$ nM |
| Silmitasertib | 1009820-21-6 | 24748573 | $IC_{50} > 1000$ nM |
| SNS314 | N/A | 16047143 | $IC_{50} > 1000$ nM |
| K00596a | 873225-46-8 | 9549298 | $IC_{50} = 100$ nM |
| GSK-3 Inhibitor IX | 667463-62-9 | 5287844 | $IC_{50} = 100$ nM |
| Baricitinib | 1187594-09-7 | 44205240 | $IC_{50} > 1000$ nM |
| (5Z)-7-Oxozeaenol | 66018-38-0 | N/A | $IC_{50} = 1000$ nM |
| CP673451 | 343787-29-1 | 10158940 | $IC_{50} > 1000$ nM |
| SureCN10063060 | N/A | 52936621 | $Ki > 1000$ nM |
| SB203580 | 152121-47-6 | 176155 | $Kd = 1100$ nM |
| SureCN5632345 | N/A | 44593646 | $Kd < 1250$ nM |
| SureCN7018367 | N/A | 18792927 | $Kd < 1250$ nM |
| IKK-2 Inhibitor IV | 507475-17-4 | 9903786 | $Kd < 1250$ nM |

TABLE IV

Exemplary JNK3 Inhibitors

| Description | CAS No. | PubChem CID | Parameter (nM) |
|---|---|---|---|
| Hesperadin | 422513-13-1 | 10142586 | $Kd < 10$ nM |
| SureCN7018367 | 312917-37-6 | 18792927 | $Kd < 10$ nM |
| Lestaurtinib | 111358-88-4 | 126565 | $Kd = 12$ nM |
| Kinome_3027 | N/A | 11640926 | $Ki = 18$ nM |
| 1,9-Pyrazoloanthrone | 129-56-6 | 8515 | $Kd = 22$ nM |
| SB203580 | 152121-47-6 | 176155 | $Kd = 35$ nM |
| JNKIN7 | N/A | 57340685 | $IC_{50} < 40$ nM |
| JNKIN8 | N/A | 57340686 | $IC_{50} < 40$ nM |
| SB202190 | 152121-30-7 | 5353940 | $Kd = 42$ nM |
| KW2449 | 1000669-72-6 | 11427553 | $Kd = 51$ nM |
| JNK Inhibitor VIII | 894804-07-0 | 11624601 | $Ki = 52$ nM |
| TTT-3002 | N/A | N/A | $IC_{50} < 60$ nM |
| Doramapimod | 285983-48-4 | 156422 | $Kd = 62$ nM |
| NVP-TAE684 | 761439-42-3 | 16038120 | $Kd = 67$ nM |
| AS601245 | 345987-15-7 | 11422035 | $IC_{50} = 70$ nM |
| CHEMBL1788116 | N/A | 11422034 | $IC_{50} = 70$ nM |
| AT9283 | 1092788-83-4 | 24905142 | $IC_{50} > 100$ nM |
| Staurosporine aglycone | 99533-80-9 | 3035817 | $IC_{50} < 100$ nM |
| 7-hydroxystaurosporine | 112953-11-4 | 72271 | $IC_{50} > 100$ nM |
| MK5108 | 1010085-13-8 | 24748204 | $IC_{50} > 100$ nM |
| Staurosporine | 62996-74-1 | 5279 | $Kd = 110$ nM |
| Kinome_2553 | N/A | 16007116 | $IC_{50} = 120$ nM |
| GSK1838705A | 1116235-97-2 | 25182616 | $Kd = 130$ nM |
| AMG-47a | 882663-88-9 | 16086114 | $IC_{50} = 145$ nM |
| JNK Inhibitor IX | 312917-14-9 | 766949 | $IC_{50} = 200$ nM |
| TG101348 | 936091-26-8 | 16722836 | $Kd = 200$ nM |
| JNJ-28312141 | 885692-52-4 | N/A | $Kd = 240$ nM |
| Nintedanib | 928326-83-4 | 9809715 | $Kd = 270$ nM |

TABLE IV-continued

Exemplary JNK3 Inhibitors

| Description | CAS No. | PubChem CID | Parameter (nM) |
|---|---|---|---|
| Gö6976 | 136194-77-9 | 3501 | $IC_{50} > 300$ nM |
| AC1NS4N8 | N/A | 23649240 | $Kd < 400$ nM |
| Syk Inhibitor IV | 732983-37-8 | 10200390 | $IC_{50} < 400$ nM |
| PDK1/Akt/Flt Inhibitor | 331253-86-2 | 5113385 | $IC_{50} = 500$ nM |
| CZC-25146 | 330003-04-7 | N/A | $IC_{50} < 600$ nM |
| R406 | 841290-81-1 | 11984591 | $IC_{50} < 600$ nM |
| GSK650394A | 890842-28-1 | 25022668 | $IC_{50} > 600$ nM |
| Momelotinib | 1056634-68-4 | 25062766 | $IC_{50} < 750$ nM |
| AST-487 | 630124-46-8 | 11409972 | $Kd = 760$ nM |
| VX702 | 745833-23-2 | 10341154 | $Kd = 780$ nM |
| HG-9-91-01 | N/A | N/A | $IC_{50} < 800$ nM |
| Ruboxistaurin | 169939-94-0 | 153999 | $IC_{50} > 900$ nM |
| GSK-3 Inhibitor IX | 667463-62-9 | 5287844 | $IC_{50} > 900$ nM |
| A 443654 | 552325-16-3 | 10172943 | $IC_{50} > 900$ nM |
| HG-10-102-01 | 1351758-81-0 | N/A | $IC_{50} = 1000$ nM |
| WZ3146 | 1214265-56-1 | 44607360 | $Kd > 1000$ nM |
| WZ4002 | 213269-23-8 | 44607530 | $Kd > 1000$ nM |
| Syk Inhibitor | 622387-85-3 | 6419747 | $IC_{50} = 1000$ nM |
| SGI-1776 | N/A | N/A | $IC_{50} > 1000$ nM |
| Silmitasertib | 1009820-21-6 | 24748573 | $IC_{50} > 1000$ nM |
| SNS314 | N/A | 16047143 | $IC_{50} > 1000$ nM |
| K00596a | 873225-46-8 | 9549298 | $IC_{50} = 1000$ nM |

A therapeutically effective amount of a small molecule inhibitor (SMI), such as a protein kinase inhibitor, may vary depending upon the route of administration and dosage form. Effective amounts of SMIs typically fall in the range of about 0.0001 to 1000 mg/kg/day, typically 0.001 to 100 mg/kg/day, and more typically in the range of about 0.01 up to 10 mg/kg/day. In some embodiments, the SMI is administered to a subject in an amount less than any of the following daily doses (mg/kg): 100, 50, 10, 5.0, 1.0, 0.5 or 1. In some embodiments, the SMI is administered to a subject in an amount greater than any of the following daily doses (mg/kg): 0.001, 0.005, 0.01, 0.05, 0.1 or 0.5. That is, the daily dose (mg/kg) can be any of a range of having an upper limit of 100, 50, 10, 5.0, 1.0, 0.5 or 1, and an independently selected lower limit of 0.001, 0.005, 0.01, 0.05, 0.1 or 0.5, wherein the lower limit is less than the upper limit. Thus, the actual amount per day for an adult mammal weighing 70 kg is typically between 0.07 and 7,000 mg, or more typically between 0.7 and 700 mg, where this amount can be administered as a single dose per day or as a series of part-doses (such as, for example, two, three, four, five or six) per day, so that the total daily dose is the same.

Typically, the SMI is selected to provide a formulation that exhibits a high therapeutic index. The therapeutic index is the dose ratio between toxic and therapeutic effects, which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

In some embodiments a SMI, such as a protein kinase inhibitor, is in the form of a pharmaceutically acceptable salt. For instance, when the SMI has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., formic acid, acetic acid, fumaric acid, oxalic acid, tartaric acid, lactic acid, maleic acid, citric acid, succinic acid, malic acid, methanesulfonic acid, benzenesulfonic acid, and p-toluenesulfonic acid) or acidic amino acids (such as aspartic acid and glutamic acid). Alternatively, when the SMI has an acidic group, such as for example, a carboxylic acid group, it can form salts with metals, such as alkali and earth alkali metals (e.g., sodium, lithium, potassium, calcium, magnesium, zinc), ammonia, organic amines (e.g., trimethylamine, triethylamine, pyridine, picoline, ethanolamine, diethanolamine, triethanolamine), or basic amino acids (e.g., arginine, lysine and ornithine).

In a preferred embodiment, a SMI, such as a protein kinase inhibitor, is contained within a pharmaceutical composition. A preferred pharmaceutical composition is a single dosage form for oral administration, such as a tablet or capsule. A pharmaceutical composition in the form of a tablet suitable for oral administration can comprise one or more pharmaceutically acceptable carriers and/or excipients suitable (e.g., inactive ingredients). Exemplary carriers include but are not limited to lactose, cellulose (for example microcrystalline cellulose), and mannitol. Exemplary excipients include but are not limited to binding agents such as hydroxypropylmethylcellulose or povidone(polyvinylpyrollidone), lubricants such as magnesium stearate, and disintegrants such as sodium starch glycollate, croscarmellose sodium, or crospovidone (cross-linked polyvinylpyrollidone).

In some embodiments, kinase inhibitor formulations are comprised of at least two SMIs having high bioavailability (>20%) are administered to a population of malaria-infected patients. Particularly preferred SMIs have an $EC_{50}$<10 nM in vitro and a single-digit mg/kg activity $ED_{90}$ in a human erythrocyte-engrafted SCID mouse model. The kinase inhibitor formulations are either single-drug formulations comprising an SMI as the only active ingredient, or as a multi-drug formulation comprising a first SMI and a second SMI. The patient population is comprised of both children (over six months of age) and adults with confirmed and uncomplicated *Plasmodium* infection who are able to swallow oral medication. The patient pool does not exclude G6PD-deficient patients.

Patients receive the orally-available kinase formulations at an effective dose over the course of the study, during which the adequate clinical and parasitological response (ACPR) and the clinical parasite reduction ratio (PRR) are monitored. The study may range from 28 up to or over 48 days, with patients exhibiting a clinical efficacy at day 28 from a single dose (or a few doses) of the kinase formulation, measured as a PRR of over 50%.

The formulations described herein are also suitable for administration as prophylactic treatments in uninfected individuals traveling to a malaria-endemic area.

Modified Kinase Inhibitors

Cell signaling connects immunity and basic intermediary metabolism at the mitochondrial level (Arnoult et al. EMBO REP 12:901-10, 2011). The links between mitochondria and host defense include modulation of bioenergetics by several protein kinases (PKs) (e.g., PKC, ERK, JNK, and p38 MAPK) (Horbinski and Chu, Free Radic Biol Med, 38:2-11, 2005) following PK activation/translocation to mitochondria in response to immune stimuli. As determined during development of the present disclosure, inhibition of mosquito p38 MAPK significantly reduces malaria parasite development. Without being bound by theory, the inhibition of parasite development is thought to be in response to p38 MAPK-regulated changes in mosquito midgut mitochondrial bioenergetics.

Some of the phosphorylation-dephosphorylation events that cells undergo when challenged with immune stimuli are not necessarily related to mitochondria-driven apoptosis, but to bioenergetics. These latter effects have been ascribed to the translocation and/or activation of critical PK within mitochondria. Thus, it would be advantageous to modify SMIs so as to redirect their localization to the mitochondrial compartment. The modified SMIs may result in less drug resistance, catabolism, and off-target effects relative to unmodified SMIs that localize to the cytosolic space (Mourtada et al., PLoS One, 8:e60253, 2013).

Suitable modifications to direct delivery of a SMI to a mitochondria include attachment of the SMI to a mitochondrial-targeting moiety, including but are not limited to lipophilic cations, mitochondrial-penetrating peptides, mitochondrial-targeting dyes, liposomes, and nanoparticles (see, e.g., Rin Jean et al., ACS Chem Biol, 9:323-333, 2014). Exemplary lipophilic cations include but are not limited to triphenylphosphonium (TPP)(Ross et al., Biochemistry, 70:222-230, 2005), AAI (Sun et al., Cancer Res, 54:1465-1471, 1994), and MKT-077 (Weisberg et al., Cancer Res, 56:551-555, 1996). Exemplary mitochondrial-penetrating peptides include but are not limited to SS-31 (Zhao et al., J Biol Chem, 279: 34682-34690, 2004), MPP (Horton et al., Chem Biol 15: 375-382, 2008), and those including 8-15 hydroxyl-containing (Serine, Threonine), positively charged amino acids (Arginine, Lysine) or hydrophobic natural and synthetic amino acids (Phenylalanine, Cyclohexylalanine; Horton et al., Chem Biol, 15:375-82, 2008; Yousif et al., Chembiochem, 10:1939-50, 2009). Exemplary mitochondrial-targeting dyes include but are not limited to rhodamine and the dyes listed in Table V.

TABLE V

Mitochondrial Targeting Dyes

| Dye | Description |
|---|---|
| 4-Di-1-ASP (DASPMI) | 4-(4-(Dimethylamino)-styryl)-N-methylpyridinium iodide |
| DASPEI | 2-(4-(dimethylamino)styryl)-N-ethylpyridinium iodide |
| Dihydrorhodamine 123 | Reduced form of Rhodamine 123 |
| Dihydrorhodamine 123, dihydrochloride | Reduced form of Rhodamine 123 |
| JC-1 chloride | Membrane potential-dependent mitochondrial stain |
| JC-1 iodide | Membrane potential-dependent mitochondrial stain |
| MitoGreen | Green-fluorescent mitochondrial dye |
| MitoRed | Red-fluorescent mitochondrial dye |
| Nonyl Acridine Orange (NAO) | Membrane potential-independent mitochondrial stain |
| Rhodamine 123 | Green-fluorescent mitochondria stain |
| Tetrabromorhodamine 123, bromide | Green-fluorescent mitochondria stain |
| TMRE | Tetramethylrhodamine ethyl ester, perchlorate; membrane potential-sensitive dye |
| TMRM | Tetramethylrhodamine methyl ester, perchlorate; membrane potential-sensitive dye |

Another strategy for modification of SMIs for use in the methods and compositions of the present disclosure involve the use of bifunctional inhibitors. These inhibitors tend to be more effective than those solely directed towards either the ATP binding site (Hu et al., Drug Discovery Today, 1:438-447, 1996) or the substrate-binding site (Lee et al., J Am Chem Soc, 126:3394-3395, 2004) because they are directed to both the ATP and substrate binding sites (Ricouart et al., J Med Chem, 34:73-78, 1991). The use of bisubstrate analog inhibitors has been described and applied to several kinases (Parang et al., Nature Structural Biology, 8:37-41, 2001;

Parang and Cole, Pharmacology & Therapeutics, 93:145-157, 2002; Hines et al., Bioorganicchemistry, 33:285-297, 2005; Broom, J Med Chem, 32:2-7, 1989; and Lee et al., Chembiochem, 9:507-509, 2008), including PKCs (van Wandelen et al., ACS Chemical Biology, 8:1479-1487, 2013; van Ameijde et al., Organic & Biomolecular Chemistry, 8:1629-1639, 2010; and Poot et al., Chembiochem, 10:2042-2051, 2009), but never targeted specifically to mitochondria. A recent review cited lack of PKC isozyme selectivity and problematic delivery as reasons why, even after over 20 years of development, the full therapeutic potential of PKC has not yet been realized (Villalba and Altman, Current Cancer Drug Targets, 2:125-137, 2002). In some embodiments, bifunctional protein kinase inhibitors are targeted to mitochondria.

Combination Therapies

The present disclosure further provides methods for treating or preventing malaria comprising administering at least one kinase inhibitor and an additional antimalarial (e.g., a compound that is not a kinase inhibitor) to a subject in need thereof under conditions suitable for treating or preventing malaria. In some embodiments, the kinase inhibitor and the antimalarial are present in a single formulation, while in other embodiments the kinase inhibitor and the antimalarial are present in separate formulations. In some embodiments, the additional antimalarial comprises one or more compounds of the antimalarial classes selected from the group consisting of amino alcohols, aminoquinolines, antibiotics, antifolates, endoperoxides, sulfonamides, and others (see, e.g., Delves et al., PLoS Medicine, 9(2) e1001169, 2012).

In particular, the additional antimalarial compound(s) may be aminoquinolines (including, but not limited to, amodiaquine, naphthoquine, AQ-13, tert-butyl isoquine, hydroxycholoquine, pyronaridine, diethylprimaquine, bulaquine, primaquine, tafenoquine, piperaquine, NPC-1161B, and chloroquine), antibiotics (including, but not limited to, azithromycin, trimethoprim, trimethoprim-sulphamethoxazole, tetracycline, mirincamycin, doxycycline, thiostrepton, fosmidomycin, and clindamycin), endoperoxides (including, but not limited to, artemeter, artesunate, OZ439, OZ277, artemisinin, artemisone, and dihydroartemisinin), antifolates (such as pyrimethamine, proguanil, dapsone, cycloguanil, P218, and chlorproguanil), sulfonamides (such as sulfadoxine, sulfadiazine, and sulfmethoxazole), amino alcohols (such as lumefantrine, halofantrine, mefloquine, and quinine), or other antimalarial drugs (including, but not limited to, DSM1, DSM265, P218, BCX4945, synthetic peroxides, methylene blue, riboflavin, pentamidine, DHEA, cycloheximide, atovaquone, deferoxamine, and N-acetyl-D-penicillamine). In some embodiments, the combination therapy includes a fixed-dose artemisinin combination therapy. In some aspects, the artemisinin combination therapy is comprised of one or more kinase inhibitor as well as one or more of artemether, artesunate, dihydroartemisinin, artemisone, and artemisinin.

In some embodiments, the additional antimalarial counteracts the malarial parasite at the same life stage(s) as the kinase inhibitor. In other embodiments, the additional antimalarial counteracts the malarial parasite at a different life stage from the kinase inhibitor.

Treatment of Infections by Other Protozoan Parasites

In other embodiments, the use of SMIs directed to mammalian kinase pathways is applied to diseases caused by other intracellular parasitic protozoa. A large number of protozoal pathogens spend a portion of their life cycle in a mammalian host, (e.g., human). Diseases caused by infection with other intracellular parasitic protozoa are also treated or prevented by mammalian kinase inhibitors. In particular, the present disclosure provides kinase inhibitors and methods for use thereof in mammalian subjects infected with a protozoan parasite selected from the group consisting of *Giardia lamblia, Cryptosporidium parvum, Cyclospora cayetanensis, Entamoeba histolytica, Trichomonas tenax, Trichomonas hominis, Trichomonas vaginalis, Trypanosoma brucei gambiense, Trypanosoma brucei rhodesiense, Trypanosoma cruzi, Leishmania donovani, Leishmania tropica, Leishmania braziliensis, Pneumocystis pneumonia, Toxoplasma gondii, Theileria lawrenci,* and *Theileria parva.* In preferred embodiments, the protozoan parasite is vectored by an arthropod (e.g., sand fly-transmitted *Leishmania*, tick-borne *Babesia microti*, kissing bug-transmitted *Trypanosoma cruzi*, tsetse-transmitted *Trypanosoma brucei*), and the SMI is directed to mammalian and arthropod kinase pathways. In some embodiments, the disease is Chagas disease, caused by infection with *Trypanosoma cruzi*. In general, the present disclosure provides methods for use of kinase inhibitors in hosts infected with a protozoan parasite.

General Techniques

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989); Oligonucleotide Synthesis (Gait, ed., 1984); Animal Cell Culture (Freshney, ed., 1987); Handbook of Experimental Immunology (Weir & Blackwell, eds.); Gene Transfer Vectors for Mammalian Cells (Miller & Calos, eds., 1987); Current Protocols in Molecular Biology (Ausubel et al., eds., 1987); PCR: The Polymerase Chain Reaction, (Mullis et al., eds., 1994); Current Protocols in Immunology (Coligan et al., eds., 1991); The Immunoassay Handbook (Wild ed., Stockton Press NY, 1994); Bioconjugate Techniques (Hermanson, ed., Academic Press, 1996); and Methods of Immunological Analysis (Masseyeff, Albert, and Staines, eds., Weinheim: VCH Verlags gesellschaft mbH, 1993).

Definitions

As used herein, the singular form "a", "an", and "the" includes plural references unless indicated otherwise. For example, "an" excipient includes one or more excipients.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting" and/or "consisting essentially of" aspects and embodiments.

The terms "small molecule inhibitor" and "SMI" refer to an organic compound (e.g., JNK inhibitor SP600125) of low molecular weight (e.g., less than 900 Daltons, preferably less than 500 Daltons, unless bound to a mitochondrial-targeting moiety in which case the size could be >2 kDa but less than 5 kDa) that inhibits a biological process. Biopolymers such as nucleic acids, proteins, and polysaccharides of greater than 10 kDa are not small molecules, although the nucleotide, amino acid, and saccharide constituents are small molecules.

The term "mitochondrial-targeting moiety" refers to a functional group of a compound that directs the compound to the mitochondria or to a specific compartment therein. Examples of mitochondrial-targeting moieties include but are not limited to lipophilic cations, mitochondrial-penetrating peptides, mitochondrial-targeting dyes, liposomes and nanoparticles.

Administration a protein kinase inhibitor in combination with an additional protein kinase inhibitor or an additional antimalarial drug includes simultaneous (concurrent) and consecutive administration in any order.

An "effective amount of" or "under conditions effective for" refers to administration of a protein kinase inhibitor in an amount sufficient to carry out a specifically stated purpose. An "effective amount" may be determined empirically and in a routine manner, in relation to the stated purpose.

The term "therapeutically effective amount" refers to an amount of an agent (e.g., protein kinase inhibitor) effective to "treat" a disease or disorder in a subject (e.g., a mammal such as a human). In the case of malaria, the therapeutically effective amount of the agent reduces a sign or symptom of malaria.

The terms "treating" or "treatment" of a disease refer to executing a protocol, which may include administering one or more drugs to an individual (human or otherwise), in an effort to alleviate signs or symptoms of the disease. Thus, "treating" or "treatment" does not require complete alleviation of signs or symptoms, does not require a cure, and specifically includes protocols that have a measurable effect on the individual.

As used herein, and as well-understood in the art, "treatment" is an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The terms "reduce" and "reduction" as used in reference to biological function (e.g., kinase activity, parasite development, etc.) refer to a measurable decrease in the function by preferably at least 50%, more preferably at least 75% and most preferably at least 90%. Depending upon the function, the reduction may be from 10-fold to 1,000,000-fold, or from 10, 100 or 1000-fold to 10,000, 100,000 or 1,000,000-fold.

EXAMPLES

Abbreviations: ACPR (adequate clinical and parasitological response); AMAS (amastigote); HTS (high throughput screen); JNK (c-Jun N terminal kinase); MAPK (mitogen-activated protein kinase); PI3K (phosphoinositide 3-kinase); PKB (protein kinase B); PKC (protein kinase C); SMI (small molecule inhibitor); TRYP (trypomastigote).

Example 1: Screening Compounds for Effects on Cell Viability, Proliferation and Kinase Activity in Mosquito Cells In Vitro and In Vivo Testing with immortalized *Anopheles* cells. Multiple cell lines created from minced mosquito embryos or larvae are available from *Anopheles stephensi* (ASE, MSQ43) and from *Anopheles gambiae* (4a3B, SUA). These cells are not derived from specific tissues, but rather were selected because they grew continuously under culture conditions after isolation. In general, these cells are phagocyte-like and immune-responsive, but cellular physiology is more muscle cell-like (Giulivi et al., Biochem J, 415:309-16, 2008). Small molecule inhibitors (SMIs) are analyzed using these cells first to establish concentration ranges that inhibit target protein kinases without toxic effects on mosquito cells.

Cell death assay. SMIs are diluted over a log-range for toxicity analyses. Assays against mosquito cells are performed in 96 well plates using CytoTox 96® Non-Radioactive Cytotoxicity Assay (Promega).

Cell doubling time assay. SMIs are diluted over a log-range to assay effects on mosquito cell doubling time (about 22 h). Assays are performed in 96 well plates using CellTiter 96® Aqueous Non-Radioactive Cell Proliferation Assay (Promega).

In vitro kinase inhibition assays. HTSs (high-throughput screens) of candidate SMIs are performed against *Anopheles* sp. recombinant kinases (e.g., PKCs, JNK, and p38 MAPK). IMAP immobilized metal ion-affinity fluorescence polarization (Molecular Devices) is used to screen 10,000 kinase-focused collection compounds (Cancer Research Technology) at 30 µM. An exemplary HTS uses 10 pM of the kinase, 100 nM 5-FAM (fluorescein-amidite)-labeled peptide, and 30 µM ATP in a buffer consisting of 20 mM Hepes (pH 7.5), 10 mM $MgCl_2$, 1 mM DTT and 0.25 mM EGTA as described (Kjaer et al., Biochem J, 451:329-342, 2013). SMIs with low $IC_{50}$ (<2 µM) are further tested using the Millipore KinaseProfiler™ service (Millipore) or Kinomescan™ (Discoverx) to determine the selectivity of key compounds against a panel of kinases (human and predicted mosquito). A preferred SMI targets overlapping but diverse kinase-mediated pathways.

Cellular kinase inhibition assays. Conserved PKCs (Pakpour et al., PLoS One, in review) and MAPKs control malaria parasite development in *A. stephensi* (ERK: Surachetpong et al. 2009 PLoS Pathog. 5(4):e1000366; p38 MAPK and JNK, unpublished data). The present disclosure is based on the understanding that SMIs against conserved kinases ingested in a blood meal containing malaria parasites from a treated human host will alter mosquito signaling to kill ingested parasites. SMI dilutions that are not toxic are assayed against mosquito cells in 96 well plates. Synthetic peptide targets (MARCKS peptide MO2-58 for cPKC, PKC-delta, PKC-epsilon; sc-3108 peptide for PKC-zeta; sc-3106 for PKC-mu or PKD) are used to distinguish effects of SMIs on PKC activity in *Anopheles* cells. Synthetic peptide targets (ERKtide, p38 substrate P03-58 or MK-2, and JNK substrate c-Jun) are used to distinguish effects of SMIs on MAPK activity in *Anopheles* cells. Briefly, cells are treated with SMIs, lysed and prepared for dot blot analysis of kinase activity analyses through detection of phosphorylation of appropriate substrates. GENBANK Accession Nos. of representative *Anopheles gambiae* kinase sequences are provided in Table 1-1.

TABLE 1-1

Mosquito Kinase Sequences

| Kinase | Type | Accession No. |
| --- | --- | --- |
| cPKC | conventional PKC | EAA0266.4 |
| nPKC-delta | novel PKC | EDO64332.2 |
| nPKC-epsilon | novel PKC | EAA07888.5 |

TABLE 1-1-continued

Mosquito Kinase Sequences

| Kinase | Type | Accession No. |
| --- | --- | --- |
| aPKC-zeta | atypical PKC | EAA00497.3, EAA00702.3 |
| PKD | protein kinase D | EAA06222.6 |
| PKN | PKC-like | EAA03911.6 |
| JNKa | c-Jun N terminal kinase | EAA03630.4, GI: 157020897 |
| JNKb | c-Jun N terminal kinase | EAA05905.3, GI: 116131141 |
| p38 MAPK | mitogen-activated protein kinase | EAA00194.4, GI: 157013175 |

Example 2: Screening Compounds for Effects on *Plasmodium* Growth, Infectivity and Development in Erythrocytes, Mice and Mosquito Cells

*Plasmodium* growth and mammalian infection assays. In order to attribute SMI activity to effects on mosquito signaling proteins specifically, SMIs are routinely screened for growth effects on *P. falciparum* parasites maintained in human erythrocyte culture in vitro. Because parasites are ingested by mosquitoes in the formed of infected erythrocytes, testing SMIs against parasite-infected erythrocytes in vitro provides insight as to whether an SMI of interest affects only the mosquito host or affects both the mosquito host and malaria parasite biology. While SMI effects on the mosquito can all be beneficial in terms of transmission reduction, beneficial effects of SMIs for the malaria patient would necessarily depend on the demonstration of an effect of the SMI on parasite growth in erythrocytes.

*P. falciparum* growth assay. Aliquots of ring stage *P. falciparum* NF54 culture are synchronized using sorbitol 48 h prior to the assay and then plated in 96-well flat-bottom plates in complete RPMI 1640 with HEPES, hypoxanthine, and 10% heat-inactivated human serum. Parasites are treated with an SMI of interest or with an equivalent volume of dimethyl sulfoxide (DMSO) diluent for 50 h in a candle jar in a 37° C. incubator. The assays are terminated by replacing the culture medium with RPMI 1640 with 10% formaldehyde in PBS. Erythrocytes are stained with 10 µg of propidium iodide/ml in phosphate buffered saline (PBS) for 1-2 h at room temperature. Infected RBCs are counted with a flow cytometer. The levels of parasite growth in response to treatment are normalized to DMSO controls, which are set to 100%. (see e.g., Pakpour et al., Infect Immun, 80:2141-9, 2012; and Drexler et al., J Exp Biol, 216:208-17, 2013). For SMIs or combinations of SMIs with an effect on parasite growth, analyses of target erythrocyte kinase(s) are completed (see, e.g., Millholland et al., Cell Host Microbe, 13:15-28, 2013).

*Plasmodium yoelii yoelii* 17XNL infection assay in mice. An established murine malaria model is used to assess effects of SMIs on *P. y. yoelii* in vivo (Luckhart et al., PLoS Pathog, 9(2):e1003180, 2013; and Chau et al., Infect Immun, 2013 Epub ahead of print). Parasitemias predictably follow a temporal rise that can reach high levels (10-15% infected of total erythrocytes) with significant detectable pathology to a variety of organs. With GFP-tagged *P. y. yoelii* 17XNL, parasite densities in mouse blood are analyzed using a fluorescence plate reader (96 well plate). Although GFP emission of parasites through live tissue and skin is low, parasite loads can be quantified as described in sampled blood from live mice and in the mouse body following infection with *P. y. yoelii* 17XNL labeled with GFP-luciferase (obtained from Dr. S. Kappe and described in Miller et al., PLoS ONE, 8(4): e60820, 2013). The bioluminescent signal in live mice infected with *P. y. yoelii*-GFP-luciferase blood stage parasites is intense in the spleen and the lungs, perhaps due to parasite sequestration in these tissues. Quantification of blood parasitemia using a fluorescence plate reader and of parasite burden in live mice using whole body imaging facilitates high throughput analyses of parasite infection over time using various doses of SMIs.

High throughput studies are initiated in the mouse model with IP injection of known SMI doses. To assess treatment, SMI formulations are administered daily by IP injection for 1-4 days to *Plasmodium*-infected mice. To assess prophylaxis, SMI formulations are administered daily by IP injection for 3-4 days to mice prior to *Plasmodium* infection. The effects of SMIs on parasitemia and disease severity over time is then assessed. If a SMI is bioactive against parasite infection, oral bioavailability is established. The same types of studies of are performed with orally delivered SMIs or control compounds to establish efficacy against infection and disease, as well as to determine pharmacokinetics in blood by high-performance chromatography and/or mass spectrometry of parent compounds.

*Plasmodium* growth and development in *A. stephensi*. A strain of *P. falciparum* that expresses GFP only in sexual stage parasites is used to monitor gametocyte ingestion and development within the first 24-32 h following feeding by *A. stephensi* (Luckhart et al., PLoS Pathog, 9(2):e1003180, 2013). In a similar way, development of oocysts (3-12 days after infection) and sporozoites (12-16 days after infection) of GFP-tagged *P. y. yoelii* 17XNL is monitored in *A. stephensi* after feeding on infected mice. The presence of sporozoites is key to understanding risk of transmission, so detection of this stage is critical to monitor transmission-blocking efficacy of SMIs. Hence, high-throughput analyses can be performed to detect and quantify infection of *A. stephensi* with both *P. falciparum* and *P. y. yoelii* 17XNL. The ability to detect (i) *P. falciparum* infection following ingestion of SMI-treated parasite culture and (ii) following feeding on SMI-treated, parasite-infected mice provides key information on SMI transmission-blocking efficacy using the best models for human and mouse parasites currently available. Following high-throughput screening for SMIs that reduce transmission, quantitative analyses of gametocytogenesis in SMI-treated *P. falciparum* culture and in SMI-treated, infected mice is used to determine if transmission-blocking effects of SMIs are due to effects on sexual stage parasite development, to SMI effects on the mosquito host signaling kinases, or both. To understand SMI effects on the mosquito host, SMI action against conserved kinase targets in mosquito tissues is examined (see, e.g., Pakpour et al., Infect Immun, 80:2141-2149, 2012; and Surachetpong et al., PLoS Pathog. 5(4):e1000366, 2009).

Figure 5:
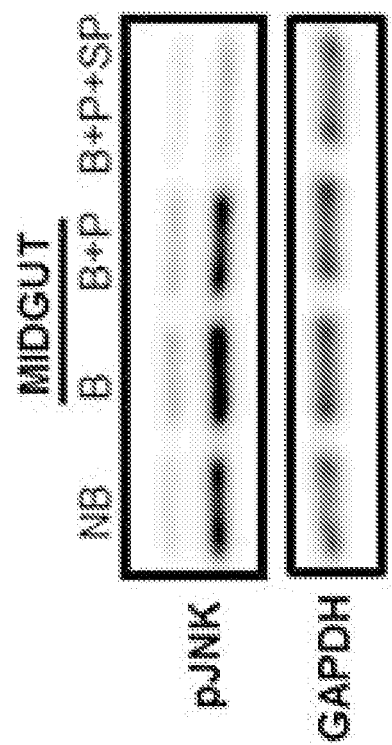
FIG. 5 shows that the midgut pJNK1/3 in *A. stephensi* is reduced after a *P. falciparum*-infected bloodmeal containing 10 μM SP600125, relative to controls. NB=no blood, B=blood, P=parasites, SP=SP600125.

Screening kinase inhibitor activity in *A. stephensi*. Addition of 10 µM SP600125 to a bloodmeal with *P. falciparum* notably decreased phosphorylation of JNK1/3 in the midgut of *A. stephensi* 3 hr after feeding relative to an identical untreated bloodmeal (FIG. 5). By comparison, provision of 1 µM SP600125 via bloodmeal resulted in a 15% reduction in midgut pJNK1/3 levels relative to controls, suggesting that relatively low levels of a JNK SMI are biologically active in *A. stephensi*.

Figure 6:
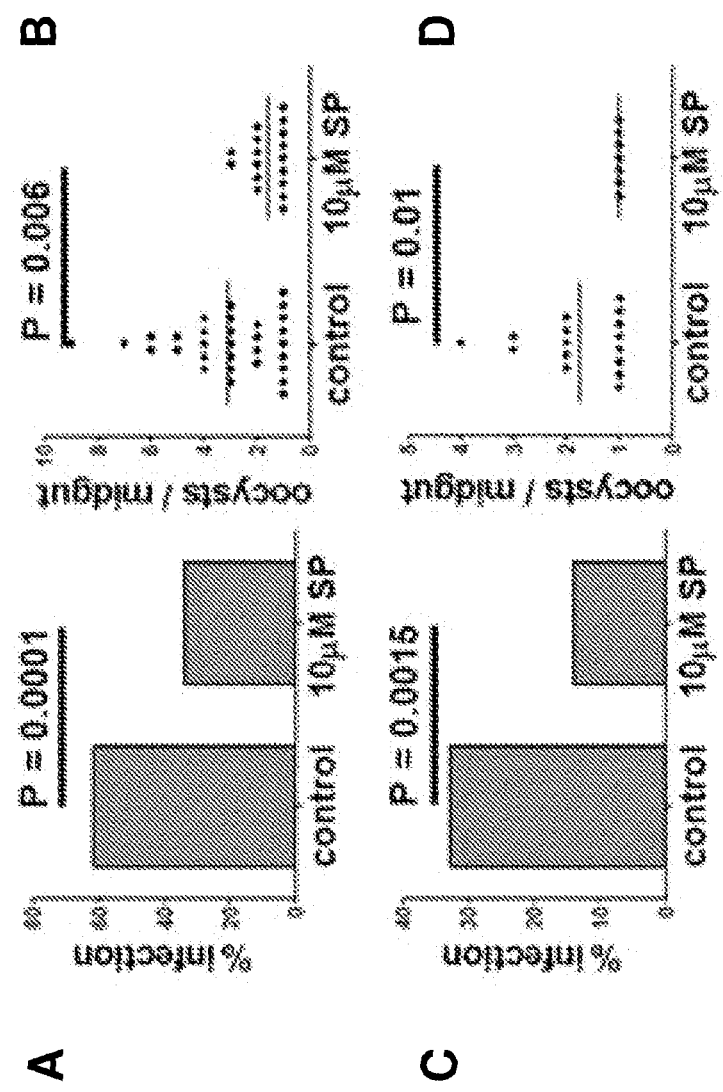
FIG. 6A-D shows the prevalence (%) and intensity (mean oocysts/midgut) of *P. falciparum* infection in two separate cohorts of *A. stephensi* (n=50) is reduced after a *P. falciparum*-infected bloodmeal containing 10 μM SP600125, relative to controls.
Figure 7:
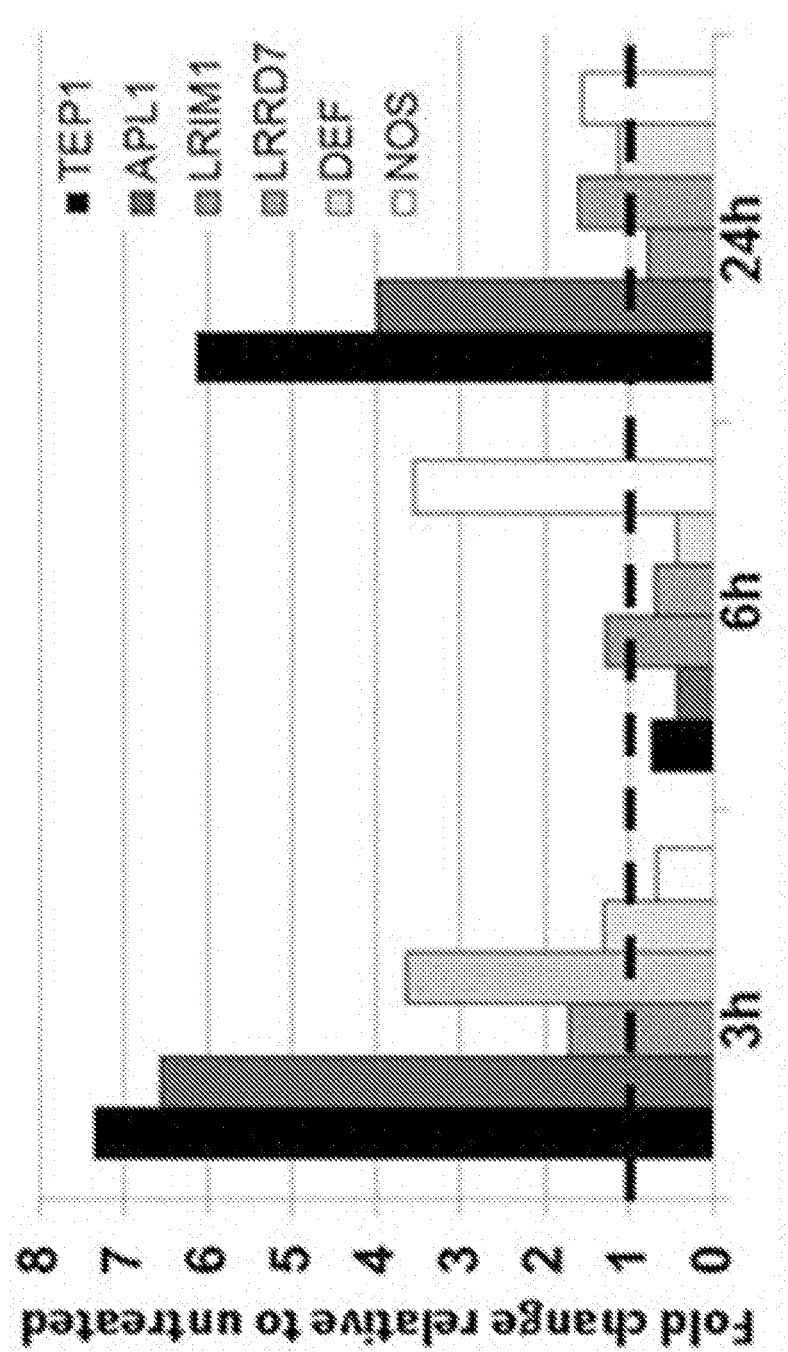
FIG. 7 shows the fold change in midgut mRNA expression levels of complement-like immune factors (TEP1, APL1, LRIM1), a leucine-rich repeat gene (LRRD7), defensin (DEF), and nitric oxide synthase (NOS) following a bloodmeal containing 10 μM SP600125, relative to an untreated control bloodmeal (set at 1, dashed line). n=2 biological replicates.

When 1 µM or 10 µM SP600125 was provided to either *A. freeborni* or *A. stephensi* daily in water or once weekly via bloodmeal (with oviposition), no negative impact on lifespan was recorded for either mosquito species. In *A. stephensi* provided with a single dose of 10 µM SP600125 in a *P. falciparum*-infected bloodmeal, parasite infection prevalence in each of two cohorts (n=50), as well as infection intensity (mean oocysts in mosquitoes with at least one oocyst) was reduced (FIG. 6). The JNK inhibition of *P. falciparum* infection in *A. stephensi* was associated with enhanced expression of an array of immune genes in the mosquito midgut (FIG. 7).

Example 3: Administration of Kinase Inhibitor(s) to Human Patients to Treat Malaria This example provides a description of a clinical study among malaria-infected individuals. The clinical and parasitological response (CPR) in test subjects receiving treatment with candidate kinase inhibitor(s) (test formulation) is compared to the CPR of control subjects receiving treatment with a control formulation (placebo or comparator).

Primary Objective: to compare the proportions of test and control subjects that are free of parasites in the blood at Day 28 post-treatment.

Secondary Objective(s): to compare the proportions of test and control subjects free of parasites in the blood at Day 7 post-treatment; to compare the time of clearance of fever in test and control subjects; and to compare the time to clearance of parasites in the blood in test and control subjects.

Tertiary Objective(s); compare the responses to treatment of test and control subjects according to the World Health Organization System (see WHO 2009 Methods for Surveillance of Antimalarial Drug Efficacy), described below.

Normal, Infected Subjects. This study is a subject- and observer-blinded, randomized, controlled study of malaria-infected, but otherwise healthy, adult and children subjects (ages 6 months to 55 years) to receive oral dosing with either the test formulation or the control formulation. Subjects are stratified by age, sex and pregnancy status (where applicable) prior to randomization.

G6PD Deficient Subjects. This study is a subject- and observer-blinded, randomized, controlled study of G6PD-deficient, malaria-infected adult and children subjects (ages 6 months to 55 years) to receive oral dosing with either the test formulation or the control formulation. Subjects are stratified by age, sex and pregnancy status (where applicable) prior to randomization.

Normal and G6PD-deficient subjects are divided into groups and receive either a once-daily or twice-daily dose, given on study Day 0. Subjects receiving either the once-daily or twice-daily dosing are further divided into groups receiving dosing on Day 0, Days 0-1, Days 0-2, Days 0-3, Days 0-4, Days 0-5, Days 0-6, or Days 0-7. All subjects are asked to return at Days 1, 2, 3, 7, 14, 21, 28 and 48 for clinical evaluation and parasitemia analysis.

Study Population. Subjects are selected from among malaria-infected male and female volunteers. Inclusion and exclusion criteria met by study participants are as follows. Inclusion Criteria: infection with *Plasmodium* (including *P. falciparum, P. vivax, P. ovale, P. malariae*, and *P. knowlesi*), ability to swallow oral medication, willingness to comply with the study protocol and ability to adhere to strict dosing requirements. Exclusion Criteria: clinically debilitating illness; signs or symptoms of severe or complicated malaria; and treatment with antimalarials within the previous 7 days.

WHO Classification of Responses to Treatment. For the purpose of this analysis, possible responses to treatment include early treatment failure, late clinical failure, late parasitological failure, and adequate clinical and parasitological response (ACPR) as described (see WHO 2009 Methods for Surveillance of Antimalarial Drug Efficacy). ACPR is defined as absence of parasitemia at Day 28, in patients who did not previously meet any of the criteria of early treatment failure, late clinical failure or late parasitological failure. Early treatment failure (ETF) includes patients exhibiting severe malaria between Days 1-3 in the presence of parasitemia, parasitemia on Day 2 higher than Day 0, parasitemia on Day 3 with a temperature of greater than or equal to 37.5° C., and parasitemia on Day 3 less than or equal to 25% of that on Day 0. Late clinical failure (LCF) includes patients not exhibiting ETF who have danger signs or severe malaria in the presence of parasitemia on any day between Day 4 and Day 28, and presence of parasitemia on any day between Day 4 and Day 28 with a temperature of greater than or equal to 37.5° C. Late parasitological failure (LPF) includes patients not exhibiting ETF or LCF who have parasitemia on any day between Day 7 and Day 28 in the absence of fever (less than 37.5° C.).

Preferred test formulations have a clinical efficacy (ACPR) on Day 7 of at least 90%, more preferably at least 95% and most preferably at least 99%. In some aspects, preferred test formulations have clinical efficacy (ACPR) of at least 50% on Day 28, more preferably at least 75% and most preferably at least 95%. Additional efficacy targets are described in Burrows et al., Malaria J, 12:187, 2013.

Statistical Analyses. All statistical tests comparing demographic, patient characteristic and safety data are conducted using the Kaplan-Meier method. ACPR is measured by blood smear or polymerase chain reaction.

Example 4: Administration of Kinase Inhibitor(s) to Human Subjects to Prevent Malaria This example provides a description of a clinical study among healthy individuals traveling in malaria-endemic areas, which compares protection from malaria resulting from prophylactic treatment with candidate kinase inhibitor(s) (test formulation) to protection from malaria in control subjects receiving treatment with a control formulation (placebo or comparator).

Primary Objective: to compare the proportions of test and control subjects free of parasites in the blood at Day 28 post-treatment.

Secondary Objective(s): to compare the proportions of test and control subjects who have parasitemia in the absence of fever (less than 37.5° C.) at Day 28 post-treatment.

Normal, Non-infected Subjects. This study is a subject- and observer-blinded, randomized, controlled study of healthy adult and children subjects (ages 6 months to 55 years) at risk of contracting malaria by traveling to an endemic area to receive oral dosing with either the test formulation or the control formulation. Subjects are stratified by age, sex and pregnancy status (where applicable) prior to randomization.

G6PD Deficient Subjects. This study is a subject- and observer-blinded, randomized, controlled study of G6PD-deficient, but otherwise healthy, adult and children subjects (ages 6 months to 55 years) at risk of contracting malaria by traveling to an endemic area to receive oral dosing with either the test formulation or the control formulation. Subjects are stratified by age prior to randomization.

Subjects are divided into groups and receive either a once-daily or twice-daily dose, given on study Day 0 (1 or 2 days before entering the endemic area). All subjects are asked to obtain a parasitemia analysis and clinical evaluation at Day 28 post-treatment.

Study Population. Subjects are selected from among healthy male and female volunteers. Inclusion and exclusion criteria met by study participants are as follows. Inclusion Criteria: at risk of contracting malaria by traveling to a malaria endemic area, ability to swallow oral medication, willingness to comply with the study protocol and ability to adhere to strict dosing requirements, age over six months. Exclusion Criteria: clinically debilitating illness; signs or symptoms of severe or complicated malaria; and treatment with antimalarials within the previous 7 days.

Classification of Responses to Treatment. For the purpose of this analysis, possible responses to treatment include prophylaxis or treatment failure. Prophylaxis is defined as absence of parasitemia at Day 28 post-treatment. Treatment failure is defined as the presence of parasitemia at or before Day 28.

Preferred test formulations have a clinical efficacy (ACPR) of at least 50% on Day 28, more preferably at least 75% and most preferably at least 95%. Additional efficacy targets are described in Burrows et al., Malaria J, 12:187, 2013.

Statistical Analyses. All statistical tests comparing demographic, patient characteristic and safety data are conducted using the Kaplan-Meier method. Parasitemia is measured by blood smear or polymerase chain reaction.

Example 5: Screening Compounds for Effects on Trypanosoma Growth and Development In Vitro Amastigote Growth Assay. SMIs are screened for growth effects on *T. cruzi* parasites maintained in Vero cells in vitro. Vero cells ($1 \times 10^5$/well) seeded on round coverslips into 24-well plates are infected with bloodstream *T. cruzi* trypomastigotes (TRYP). After 24 hours of parasite-host cell interaction (10:1 parasite:cell ratio), the infected cultures are washed to remove free parasites and incubated for another 72 hours with a test SMI (1 to 10 micromolar), a placebo, or control comparator. Cell cultures are set up in triplicate and maintained at 37° C. in 5% $CO_2$. Uninfected treated cultures exposed to vehicle (1% DMSO) are used as controls. The method for determining the rate of infection of host cells by *T. cruzi* has previously been described in detail (Nakajima-Shimada et al., Antimicrob Agents and Chemo, 40:2455-2458, 1996). Briefly, host cells attached to the coverslip seeded in 24-well plate are gently rinsed with phosphate-buffered saline, air-dried, fixed in absolute methanol and stained with Giemsa. The coverslip is then transferred to a glass slide where the mounted cells are finally observed under a light microscope. The percentage of host cells with more than one amastigote (AMAS) in the cytoplasm are counted and the mean number of AMAS per infected cell is determined by analyzing a total of 400 host cells distributed in randomly chosen microscopic fields.

Trypomastigote Growth Assay. Bloodstream TRYP are subjected to treatment by incubation of $1.5 \times 10^5$ TRYP with 1-10 μM of a test SMI, a placebo, or control comparator. Parasites are diluted in RPMI 1640 medium supplemented with 10% FCS, seeded in 96-well microplates, and incubated at 37° C. in a 5% $CO_2$ atmosphere. After 24 hours, the remaining live parasites are counted in a Neubauer chamber as previously described (Fernandez et al., *Experimental Parasitology*, 124:172-180, 2010). Trypanocydal effect is determined by counting remaining TRYP at each concentration of drug with respect to a negative control group. Each assay is performed in triplicate.

Example 6: Screening Compounds for Effects on Trypanosoma Growth, Infectivity and Development in Mice At least two *T. cruzi* strains are used for the infection assay: one lethal at the acute phase and the other non-lethal at the acute phase. Use of two strains in this matter facilitates evaluation of parasitemia reduction and cure in the acute and chronic phases of infection.

Parasitemia Reduction

Groups: n=5 (6 to 8 week old mice).

Infection: Lethal strain (100 blood TRYP) injected intradermally into the hind foot pad or alternatively or by intraperitoneal inoculation.

Treatment: SMI formulations are administered daily by IP injection for 5 days to *Trypanosoma*-infected mice, starting at parasitemia levels above $10^4$ TRYP/ml of blood. Control formulations, a placebo or comparator, are tested in parallel to the SMI formulations. The effects of SMIs on parasitemia (e.g., twice weekly) and disease severity over time is then assessed. If a SMI is bioactive against parasite infection, oral bioavailability is established. The same types of studies are performed with orally delivered SMIs.

Cure at the Acute Phase

Groups: n=5 (6 to 8 week old mice).

Infection: Lethal strain (100 blood TRYP) injected intradermally into the hind footpad or alternatively by intraperitoneal inoculation.

Treatment: SMI formulations are administered daily by IP injection for 20 to 30 days to *Trypanosoma*-infected mice, starting at parasitemia levels above $10^4$ TRYP/ml of blood. Control formulations, a placebo or comparator, are tested in parallel to the SMI formulations. The effects of SMIs on parasitemia and disease severity over time is then assessed. If a SMI is bioactive against parasite infection, oral bioavailability is established. The same types of studies are performed with orally delivered SMIs. PCR may also be employed to detect AMAS in mouse tissues.

Cure at the Chronic Phase.

Groups: N=5 (6 to 8 week old mice).

Infection: Non-lethal strain injected intradermally into the hind footpad or alternatively by intraperitoneal inoculation. In particular, a fluorescently-labeled non-lethal K98 strain may be used.

Treatment: SMI formulations are administered daily by IP injection for 30 days to *Trypanosoma*-infected mice, starting at parasitemia levels above $10^4$ TRYP/ml of blood. Control formulations, a placebo or comparator, are tested in parallel to the SMI formulations. The effects of SMIs on parasitemia and disease severity over time is then assessed. If a SMI is bioactive against parasite infection, oral bioavailability is established. The same types of studies are performed with orally delivered SMIs. PCR may also be employed to detect AMAS in mouse tissues. If fluorescently labeled parasites of the non-lethal K98 strain are used, parasitemia measurements may be performed by microscopy or automated fluorescent cell counting.

Example 7: Administration of Kinase Inhibitor(s) to Human Patients to Treat Chagas Disease This example provides a description of a clinical study among *Trypanosoma cruzi*-infected individuals. The clinical and parasitological response (CPR) in test subjects receiving treatment with candidate kinase inhibitor(s) (test formulation) is compared to the CPR of control subjects receiving treatment with a control formulation (placebo or comparator).

Primary Objective: to compare the proportions of test and control subjects that are free of parasites in the blood at 12 months post-treatment.

Secondary Objective(s): to compare the proportions of test and control subjects free of parasites in the blood at Weeks 8, 16, 24, and 40 post-treatment; to compare the safety and tolerability of the candidate kinase inhibitor(s) in test and control subjects; and to compare the time to clearance of parasites in the blood in test and control subjects.

Normal, Infected Subjects. This study is a subject- and observer-blinded, randomized, controlled study of *Trypanosoma cruzi*-infected, but otherwise healthy, adult subjects (ages 18 years and older) to receive oral dosing with either the test formulation or the control formulation. Subjects are stratified by age, sex and pregnancy status (where applicable) prior to randomization.

Study Population. Subjects are selected from among *Trypanosoma cruzi*-infected male and female volunteers. Inclusion and exclusion criteria met by study participants are as follows. Inclusion Criteria: infection with *Trypanosoma cruzi*, ability to swallow oral medication, willingness to comply with the study protocol and ability to adhere to strict dosing requirements. Exclusion Criteria: clinically debilitating illness; and signs or symptoms of severe or complicated Chagas disease.

Classification of Responses to Treatment. For the purpose of this analysis, a positive response to treatment (parasitological cure) is indicated by an absence of parasites in the blood, as measured by real time polymerase chain reaction.

Statistical Analyses. All statistical tests comparing demographic, patient characteristic and safety data are conducted using the Kaplan-Meier method. Parasitological cure is measured by real time polymerase chain reaction.

We claim:

1. A method for treating or preventing malaria comprising: administering a first protein kinase inhibitor and a second protein kinase inhibitor to a mammalian subject in need thereof under conditions effective for treating or preventing malaria, wherein the first kinase inhibitor is capable of reducing activity of a first mammalian protein kinase and the second kinase inhibitor is capable of reducing activity of a second mammalian protein kinase, which is different from the first mammalian protein kinase, and wherein one or both of the first and second kinase inhibitors are capable of reducing activity of a mosquito protein kinase.

2. The method of claim 1, wherein the first and second mammalian protein kinases comprise a member of one or more families selected from the group consisting of a protein kinase C (PKC) family, a c-Jun N-terminal kinase (JNK) family, and a p38 mitogen activated protein kinase (MAPK) family.

3. The method of claim 1, wherein the first and second mammalian kinases are members of the PKC family and the MAPK family, respectively.

4. The method of claim 1, wherein the mosquito kinase comprises one or more of the group consisting of cPKC, nPKC-delta, nPKC-epsilon, aPKC-zeta, PKD, PKN, JNKa, JNKb and p38 MAPK.

5. The method of claim 1, wherein the mosquito kinase comprises aPKC-zeta.

6. The method of claim 1, wherein the subject is infected with *P. falciparum, P. vivax, P. ovale, P. malariae*, or *P. knowlesi*.

7. The method of claim 6, wherein the subject is infected with a chloroquine-resistant *Plasmodium* sp.

8. The method of claim 6, wherein the subject is experiencing one or both of chills and fever prior to the administering step.

9. The method of claim 8, wherein treating malaria comprises alleviating a symptom of malaria experienced by the subject.

10. The method of claim 6, further comprising administering an effective amount of an additional antimalarial drug to the mammalian subject.

11. The method of claim 10, wherein the additional antimalarial drug comprises one or more compounds of the antimalarial classes selected from the group consisting of amino alcohols, aminoquinolines, antibiotics, antifolates, endoperoxides, sulfonamides, and others.

12. The method of claim 1, wherein the subject is an uninfected individual planning to visit a malaria endemic area after the administering step.

13. The method of claim 12, wherein preventing malaria comprises protecting the subject from developing parasitemia during their visit to the malaria endemic area for a period of up to thirty days.

14. The method of claim 12, wherein chloroquine-resistant *Plasmodium* are known to be present in the malaria endemic area.

15. A method for treating or preventing malaria comprising: administering a protein kinase inhibitor and an additional antimalarial drug to a mammalian subject in need thereof under conditions effective for treating or preventing malaria, wherein the kinase inhibitor is capable of reducing activity of a mammalian protein kinase and a mosquito protein kinase.

16. The method of claim 15, wherein the protein kinase inhibitor comprises a first and a second protein kinase inhibitor, and wherein the first kinase inhibitor is capable of reducing activity of a first mammalian protein kinase and the second kinase inhibitor is capable of reducing activity of a second mammalian protein kinase, which is different from the first mammalian protein kinase.

17. The method of claim 15, wherein the mammalian protein kinase comprises a member of one or more families selected from the group consisting of a protein kinase C (PKC) family, a c-Jun N-terminal kinase (JNK) family, and a p38 mitogen activated protein kinase (MAPK) family.

18. The method of claim 15, wherein the mosquito kinase comprises one or more of the group consisting of cPKC, nPKC-delta, nPKC-epsilon, aPKC-zeta, PKD, PKN, JNKa, JNKb and p38 MAPK.

19. The method of claim 15, wherein the mosquito kinase comprises aPKC-zeta.

20. The method of claim 15, wherein the subject is infected with *P. falciparum, P. vivax, P. ovale, P. malariae*, or *P. knowlesi*.

21. The method of claim 20, wherein the subject is infected with a chloroquine-resistant *Plasmodium* sp.

22. The method of claim 20, wherein the subject is experiencing one or both of chills and fever prior to the administering step.

23. The method of claim 22, wherein treating malaria comprises alleviating a symptom of malaria experienced by the subject.

24. The method of claim 15, wherein the additional antimalarial drug comprises one or more compounds of the antimalarial classes selected from the group consisting of amino alcohols, aminoquinolines, antibiotics, antifolates, endoperoxides, sulfonamides, and others.

25. The method of claim 15, wherein the subject is an uninfected individual planning to visit a malaria endemic area after the administering step.

26. The method of claim 25, wherein preventing malaria comprises protecting the subject from developing parasitemia during their visit to the malaria endemic area for a period of up to thirty days.

27. The method of claim 25, wherein chloroquine-resistant *Plasmodium* are known to be present in the malaria endemic area.

28. A method of identifying an antimalarial compound, comprising:
(a) measuring activity of a mammalian protein kinase and a mosquito protein kinase in the presence and absence of a test compound; and
(b) identifying the test compound as an antimalarial compound when the activity of the mammalian protein kinase and the mosquito protein kinase is reduced in the presence as compared to the absence of the test compound.

29. The method of claim 28, further comprising growing mosquito cells in vitro in the presence and absence of the test compound and identifying the test compound as mosquito-cell safe when viability or doubling time of the mosquito cells is not significantly reduced in the presence as compared to the absence of the test compound.

30. The method of claim 29, wherein the mosquito cells are *Anopheles stephensi* or *Anopheles gambiae* cells.

31. A method of identifying an antimalarial compound, comprising:
(a) comparing development of oocysts or sporozoites in mosquitos after consumption of a bloodmeal comprising *Plasmodium* sp. in the presence and absence of a test compound; and
(b) identifying the test compound as an antimalarial compound when the development of oocysts or sporozoites is reduced in the mosquitos in the presence as compared to the absence of the test compound.

32. The method of claim 31, wherein step (b) comprises enumerating oocysts per mosquito midgut.

33. The method of claim 31, wherein the *Plasmodium* sp. is *P. falciparum* or *P. yoelii yoelii*.

34. A pharmaceutical composition comprising:
a protein kinase inhibitor attached to a mitochondrial-targeting moiety, and
one or both of a pharmaceutically acceptable excipient and carrier, wherein the protein kinase inhibitor is present in an amount effective to treat or prevent malaria in a mammalian subject.

* * * * *